United States Patent
Yu et al.

(10) Patent No.: US 12,202,899 B2
(45) Date of Patent: Jan. 21, 2025

(54) ANTI-HUMAN PD-L1 ANTIBODIES AND THEIR USES

(71) Applicant: Development Center for Biotechnology, Taipei (TW)

(72) Inventors: Cheng-Chou Yu, Taipei (TW); Shih-Rang Yang, Taipei (TW); Tsung-Han Hsieh, Taipei (TW); Mei-Chi Chan, Taipei (TW); Shu-Ping Yeh, Taipei (TW); Chuan-Lung Hsu, Taipei (TW); Ling-Yueh Hu, Taipei (TW); Chih-Lun Hsiao, Taipei (TW)

(73) Assignee: Development Center for Biotechnology, Taipei (TW)

( * ) Notice: Subject to any disclaimer, the term of this patent is extended or adjusted under 35 U.S.C. 154(b) by 895 days.

(21) Appl. No.: 17/256,999

(22) PCT Filed: Jul. 14, 2019

(86) PCT No.: PCT/US2019/041747
§ 371 (c)(1),
(2) Date: Dec. 29, 2020

(87) PCT Pub. No.: WO2020/018395
PCT Pub. Date: Jan. 23, 2020

(65) Prior Publication Data
US 2021/0139592 A1    May 13, 2021

Related U.S. Application Data

(60) Provisional application No. 62/698,096, filed on Jul. 14, 2018.

(51) Int. Cl.
*C07K 16/28* (2006.01)
*A61K 47/68* (2017.01)

(52) U.S. Cl.
CPC ...... *C07K 16/2827* (2013.01); *A61K 47/6801* (2017.08); *C07K 2317/31* (2013.01); *C07K 2317/565* (2013.01)

(58) Field of Classification Search
CPC ............... C07K 16/2827; C07K 2317/565
USPC ............................................ 424/133.1
See application file for complete search history.

(56) References Cited

U.S. PATENT DOCUMENTS 9,334,331 B2 * 5/2016 Igawa ............... A61P 7/00
10,421,807 B2 * 9/2019 Gonzales ........... A61P 17/08
10,435,470 B2 * 10/2019 Zha .................. A61P 33/00

FOREIGN PATENT DOCUMENTS

CN       115124621    *  9/2022
WO    WO 2022078520   *  4/2022

OTHER PUBLICATIONS

Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*

* cited by examiner

*Primary Examiner* — Lynn A Bristol
(74) *Attorney, Agent, or Firm* — Liang Legal Group, PLLC

(57) ABSTRACT

An anti-PD-L1 antibody, or an antigen-binding fragment thereof, comprising: a heavy chain variable region comprising the three CDRs with the sequences of SEQ ID NOs: 2-4, 6-8, 10-12, 14-16, or 18-20; and/or a light chain variable region comprising the three CDRs with the sequences of SEQ ID NOs: 22-24, 26-28, 30-32, 34-36, or 38-40, wherein the antibody is a chimeric, humanized, composite, or human antibody.

15 Claims, 16 Drawing Sheets
Specification includes a Sequence Listing.

FIG. 1A (Protein: SEQ ID NO:1; Nucleotide: SEQ ID NO: 41)

```
CAG GTC CAA CTG CAG CAG CCG GGG ACT GAG CTG GTG AAG CCT GGG          45
 Q   V   Q   L   Q   Q   P   G   T   E   L   V   K   P   G

GCT TCA GTG AAA CTG TCC TGT AAG GCT TCT GGC TAC ATC TTC ATC          90
 A   S   V   K   L   S   C   K   A   S   G   Y   I   F   I
                                         (SEQ ID NO: 2)  CDR1

AGC TTC TGG ATA CAC TGG GTG AAG CAG AGG CCT GGA CAA GGC CTT         135
 S   F   W   I   H   W   V   K   Q   R   P   G   Q   G   L

AAA TGG ATT GGT AAT ATT GAC CCT TCT GAT AGT GAA ACT CAC TAC         180
 K   W   I   G   N   I   D   P   S   D   S   E   T   H   Y
                     (SEQ ID NO: 3)  CDR2

AAT CAA AAG TTC AAG GAC AAG GCC ACA TTG ACT GTA GAC AAA TCC         225
 N   Q   K   F   K   D   K   A   T   L   T   V   D   K   S

TCC AGC ACA GCC TAC ATG CAG CTC AGC AGC CTG ACA TCT GAG GAC         270
 S   S   T   A   Y   M   Q   L   S   S   L   T   S   E   D

TCT GCG GTC TAT TAC TGT GCA AGA TTG GAT GGT GAC TAC GGG AGG         315
 S   A   V   Y   Y   C   A   R   L   D   G   D   Y   G   R
                                     (SEQ ID NO: 4)  CDR3

GCT TAC TGG GGC CAA GGG ACT CTG GTC ACT GTC TCT GCA
 A   Y   W   G   Q   G   T   L   V   T   V   S   A
```

FIG. 1B (Protein: SEQ ID NO: 5; Nucleotide: SEQ ID NO: 42)

```
CAG GTC CAA CTG CAG CAG CCT GGG GCT GAA CTG GTG AAG CCT GGG       45
 Q   V   Q   L   Q   Q   P   G   A   E   L   V   K   P   G

GCT TCA GTG AAA CTG TCC TGC AAG GCT TCT GGC TAC ATC TTC ATC       90
 A   S   V   K   L   S   C   K   A   S   G   Y   I   F   I
                                         ─────────────────
                                         (SEQ ID NO: 6) CDR1
AGC TTC TGG ATA CAC TGG GTG AAG CAG AGG CCT GGA CAA GGC CTT      135
 S   F   W   I   H   W   V   K   Q   R   P   G   Q   G   L
 ─────────────────

GAA TGG ATT GGT AAT ATT GAC CCT TCT GAT AGT GAA ACT CAC TAC      180
 E   W   I   G   N   I   D   P   S   D   S   E   T   H   Y
                 ───────────────────────────────────────
                 (SEQ ID NO: 7) CDR2
AAT GAA AAA TTC AGG GAC AAG GCC TCA TTG ACT GTA GAC AAG TCC      225
 N   E   K   F   R   D   K   A   S   L   T   V   D   K   S
 ───────────────────

TCC AGC ACA GCC TAC ATG CAG CTC AGC AGC CTG ACA TCT GAG GAC      270
 S   S   T   A   Y   M   Q   L   S   S   L   T   S   E   D

TCT GCG GTC TAT TTC TGT GCA AGG TTG GAT GGT GAC TAC GGG AGG      315
 S   A   V   Y   F   C   A   R   L   D   G   D   Y   G   R
                                     ─────────────────────
                                     (SEQ ID NO: 8) CDR3
GCT TAC TGG GGC CAA GGG ACT CTG GTC ACT GTC TCT GCA
 A   Y   W   G   Q   G   T   L   V   T   V   S   A
 ─────────
```

FIG. 1C (Protein: SEQ ID NO: 9; Nucleotide: SEQ ID NO: 43)

```
CAG GTT CAG TTG CAG CAG TCT GGA CCT GAG CTG GTG AAG CCT GGG      45
 Q   V   Q   L   Q   Q   S   G   P   E   L   V   K   P   G

GCC TCA GTG AAG ATT TCC TGC AAG GCC TCT GGC TAT GCA TTC AGT      90
 A   S   V   K   I   S   C   K   A   S   G   Y   A   F   S
                                        (SEQ ID NO: 10) CDR1

ACC TCC TGG ATA AAC TGG CTG AAG CAG AGG CCT GGA GAG GGT CTT     135
 T   S   W   I   N   W   L   K   Q   R   P   G   E   G   L

GAG TGG CTT GGA CGG ATT TAT CCT GGA GAT GGA GAT ATA AAC TAC     180
 E   W   L   G   R   I   Y   P   G   D   G   D   I   N   Y
                     (SEQ ID NO: 11) CDR2

AAT GGG AAG TTC AAG GAC AAG GCC ACA CTG ACT GCA GAC AAA TCC     225
 N   G   K   F   K   D   K   A   T   L   T   A   D   K   S

TCC AGT ACA GCC CAC ATA CAA CTC AAC AGC CTG ACA TCT GAG GAC     270
 S   S   T   A   H   I   Q   L   N   S   L   T   S   E   D

TCT GCG GTC TAC TTC TGT GCA AGA TCG AAT CAT TAC TAC TTT GAC     315
 S   A   V   Y   F   C   A   R   S   N   H   Y   Y   F   D
                                    (SEQ ID NO: 12)  CDR3

TTC TGG GGC CAA GGC ACC ACT CTC ACA GTC TCC TCA
 F   W   G   Q   G   T   T   L   T   V   S   S
```

FIG. 1D (Protein: SEQ ID NO: 13; Nucleotide: SEQ ID NO: 44)

```
CAG GTT CAG CTG CAG CAG TCT GGA CCT GAG CTG GTG AAG CCT GGG      45
 Q   V   Q   L   Q   Q   S   G   P   E   L   V   K   P   G

GCC TCA GTG AAG ATT TCC TGC AAG GCT TCT GGC TAT GCA TTC AGT      90
 A   S   V   K   I   S   C   K   A   S   G   Y   A   F   S
                                           ─────────────────
                                           (SEQ ID NO: 14) CDR1

ACC TCC TGG ATG AAC TGG GTA AAG CAG AGG CCT GGA AAG GGT CTT     135
 T   S   W   M   N   W   V   K   Q   R   P   G   K   G   L
 ─────────────────

GAG TGG ATT GGA CGG ATT TAT CCT GGA GAT GAA GAT ACT AAC TAC     180
 E   W   I   G   R   I   Y   P   G   D   E   D   T   N   Y
                 ───────────────────────────────────────────
                 (SEQ ID NO: 15) CDR2

AAT GGG AAC TTC AAG GGC AAG GCC ACA CTG ACT GCA GAC AAA TCT     225
 N   G   N   F   K   G   K   A   T   L   T   A   D   K   S
 ───────

TCC AGT ACA GCC TAT ATG CAA CTC ATC AGC CTG ACA TCT GAG GAC     270
 S   S   T   A   Y   M   Q   L   I   S   L   T   S   E   D

TCT GCG GTC TAC TTC TGT GCA AGA TCG GAT AAT TAC TAC TTT GAC     315
 S   A   V   Y   F   C   A   R   S   D   N   Y   Y   F   D
                                     ───────────────────────
                                     (SEQ ID NO: 16) CDR3

TAC TGG GGC CAA GGC ACC ACT CTC ACA GTC TCC TCA
 Y   W   G   Q   G   T   T   L   T   V   S   S
 ───
```

FIG. 1E (Protein: SEQ ID NO: 17; Nucleotide: SEQ ID NO: 45)

```
GAG GTG CAG CTG GTG GAG TCT GGG GGA GGC TTT GTG AAG CCT GGA        45
 E   V   Q   L   V   E   S   G   G   G   F   V   K   P   G

GGG TCC CGG AAA CTC TCC TGT GCA GCC TCT GGA TTC ACT TTC AGT        90
 G   S   R   K   L   S   C   A   A   S   G   F   T   F   S
                                         (SEQ ID NO: 18) CDR1

GAC TCT GGA ATG CAC TGG GTC CGT CAG GCT CCA GAG AAG GGG CTG       135
 D   S   G   M   H   W   V   R   Q   A   P   E   K   G   L

GAG TGG GTT GCA TAC ATT AGT GCT GGC AGT TAT ACC ATC TAC TAT       180
 E   W   V   A   Y   I   S   A   G   S   Y   T   I   Y   Y
                     (SEQ ID NO: 19) CDR2

GCA GAC ATA GTG AAG GGC CGA TTC ACC ATC TCT AGA GAC AGT GCC       225
 A   D   I   V   K   G   R   F   T   I   S   R   D   S   A

AAG AAC ACC CTG TTC CTG CAA ATG ACC AGT CTA AGG TCT GAG GAC       270
 K   N   T   L   F   L   Q   M   T   S   L   R   S   E   D

ACA GCC ATT TAT TAT TGT GCA AGA GGG GAC TGG TAC TTC GCT GTC       315
 T   A   I   Y   Y   C   A   R   G   D   W   Y   F   A   V
                                 (SEQ ID NO: 20) CDR3

TGG GGC GCA GGG ACC ACG GTC ACC GTC TCC TCA
 W   G   A   G   T   T   V   T   V   S   S
```

FIG. 2A (Protein: SEQ ID NO: 21; Nucleotide: SEQ ID NO: 46)

```
AAC ATT GTG CTG ACC CAA TCT CCA GCT TCT TTG GCT GTG TCT CTA      45
 N   I   V   L   T   Q   S   P   A   S   L   A   V   S   L

GGA CAG AGG GCC ACC ATA TCC TGC AGA GCC AGT GAA AGT GTT GAT      90
 G   Q   R   A   T   I   S   C   R   A   S   E   S   V   D
                                    (SEQ ID NO: 22)

AGT TTT GGC AAT AGT TTT ATG CAC TGG TAC CAG CAG AAA CCA GGA     135
 S   F   G   N   S   F   M   H   W   Y   Q   Q   K   P   G
CDR1

CAG CCG CCC AAA CTC CTC ATC TAT CTT GCA TCC AAC CTA GAA TCT     180
 Q   P   P   K   L   L   I   Y   L   A   S   N   L   E   S
                         (SEQ ID NO: 23) CDR2

GGG GTC CCT GCC AGG TTC AGT GGC AGT GGG TCT AGG ACA GAC TTC     225
 G   V   P   A   R   F   S   G   S   G   S   R   T   D   F

ACC CTC ACC ATT GAT CCT GTG GAG GCT GAT GAT ACT GCA ACC TAT     270
 T   L   T   I   D   P   V   E   A   D   D   T   A   T   Y

TAC TGT CAG CAA AAT AAT GAG GAT CCG TTG ACG TTC GGT GGA GGC     315
 Y   C   Q   Q   N   N   E   D   P   L   T   F   G   G   G
         (SEQ ID NO: 24) CDR3

ACC AAA CTG GAA ATC AAA CGG
 T   K   L   E   I   K   R
```

FIG. 2B (Protein: SEQ ID NO: 25; Nucleotide: SEQ ID NO: 47)

```
AAC ATT GCG CTG ACC CAA TCT CCA ACT TCT TTG GCT GTG TCT CAA    45
 N   I   A   L   T   Q   S   P   T   S   L   A   V   S   Q

GGG CAG AGG GCC ACC ATA TCC TGC AGA GCC AGT GAA AGT GTT GAT    90
 G   Q   R   A   T   I   S   C   R   A   S   E   S   V   D
                                 (SEQ ID NO: 26)

AGT AAT GGC AAT AGT TTT ATG CAC TGG TAC CAG CAG AAA CCA GGA   135
 S   N   G   N   S   F   M   H   W   Y   Q   Q   K   P   G
 CDR1

CAG CCA CCC AAA CTC CTC ATC TAT CTT GCA TCC AAC CTA GAA TCT   180
 Q   P   P   K   L   L   I   Y   L   A   S   N   L   E   S
                                 (SEQ ID NO: 27) CDR2

GGG GTC CCT GCC AGG TTC AGT GGC AGT GGG TCT AGG ACA GAT TTC   225
 G   V   P   A   R   F   S   G   S   G   S   R   T   D   F

ACC CTC ACC ATT GAT CCT GTG GAG GCT GAT GAT GCT GCA ACC TAT   270
 T   L   T   I   D   P   V   E   A   D   D   A   A   T   Y

TAC TGT CAG CAA AAT AAT GAC GAT CCG TGG ACG TTC GGT GGA GGC   315
 Y   C   Q   Q   N   N   D   D   P   W   T   F   G   G   G
          (SEQ ID NO: 28) CDR3

ACA AAG CTG GAA ATC AAA CGG
 T   K   L   E   I   K   R
```

FIG. 2C (Protein: SEQ ID NO: 29; Nucleotide: SEQ ID NO: 48)

```
GAT GTC CAG ATG ACA CAG ACT ACA TCC TCC CTG TCT GCC TCT CTG    45
 D   V   Q   M   T   Q   T   T   S   S   L   S   A   S   L

GGA GAC AGA GTC ACC ATC AAT TGC AGG GCA AGT GAA GAC ATT AGA    90
 G   D   R   V   T   I   N   C   R   A   S   E   D   I   R
                                     ‾‾‾‾‾‾‾‾‾‾‾‾‾‾‾‾‾‾‾‾‾‾‾
                                          (SEQ ID NO: 30) CDR1

ACT TAT TTA AAC TGG TAT CAG CAG AAA CCA GAT GGA ACT ATT AAA    135
 T   Y   L   N   W   Y   Q   Q   K   P   D   G   T   I   K
‾‾‾‾‾‾‾‾‾‾‾‾‾‾‾‾

CTC CTG ATC TAC TAC ACA TCC AGA TTA CAT TCA GGA GTC CCA TCA    180
 L   L   I   Y   Y   T   S   R   L   H   S   G   V   P   S
                 ‾‾‾‾‾‾‾‾‾‾‾‾‾‾‾‾‾‾‾‾‾‾‾‾‾‾‾‾‾
                   (SEQ ID NO: 31) CDR2

AGG TTC AGT GGC AGT GGG TCT GGA ACA GAT TAT TCT CTC ACC ATT    225
 R   F   S   G   S   G   S   G   T   D   Y   S   L   T   I

AGC AAC CTG GAC CAA GAA GAT ATT GCC ACT TAC TTT TGT CAA CAG    270
 S   N   L   D   Q   E   D   I   A   T   Y   F   C   Q   Q
                                                     ‾‾‾‾‾‾‾

GTT CAT ACA CTT CCT CCG TGG ACG TTC GGT GGA GGC ACC AAG CTG    315
 V   H   T   L   P   P   W   T   F   G   G   G   T   K   L
‾‾‾‾‾‾‾‾‾‾‾‾‾‾‾‾‾‾‾‾‾‾‾‾‾‾‾‾‾‾‾‾‾
     CDR3   (SEQ ID NO: 32)

GAA ATC AAA CGG
 E   I   K   R
```

FIG. 2D (Protein: SEQ ID NO: 33; Nucleotide: SEQ ID NO: 49)

```
GAT ATC CAG ATG ACA CAG ACT ACA TCC TCC CTG TCT GCC TCT CTG        45
 D   I   Q   M   T   Q   T   T   S   S   L   S   A   S   L

GGA GAC AGA GTC ACC ATC ACT TGC AGG GCA AGT GAT GAC ATT AGG        90
 G   D   R   V   T   I   T   C   R   A   S   D   D   I   R
                                 ─────────────────────────
                                      (SEQ ID NO: 34) CDR1

ACT TAT TTA AAC TGG TAT CAG CAG AAA CCA GAT GGA TCT GTT AAA       135
 T   Y   L   N   W   Y   Q   Q   K   P   D   G   S   V   K
 ───────────────

CTC CTG ATC TAC TAC ACA TCA AGA TTA CAC TCG GGA GTC CCA TCA       180
 L   L   I   Y   Y   T   S   R   L   H   S   G   V   P   S
                 ─────────────────────────────
                     (SEQ ID NO: 35) CDR2

AGG TTC AGT GGC AGT GGG TCT GGA ACA GAT TAT TCT CTC ACC ATT       225
 R   F   S   G   S   G   S   G   T   D   Y   S   L   T   I

AGC AAC CTG GTT CAA GAA GAT TTT GCC ACT TAT TTT TGC CAA CAG       270
 S   N   L   V   Q   E   D   F   A   T   Y   F   C   Q   Q
                                                 ───────────

GTT CAT ACG CTT CCT CCG TGG ACG TTC GGT GGA GGC ACC AAG CTG       315
 V   H   T   L   P   P   W   T   F   G   G   G   T   K   L
 ───────────────────────────────
         CDR3 (SEQ ID NO: 36)

GAA ATC AAA CGT
 E   I   K   R
```

FIG. 2E (Protein: SEQ ID NO: 37; Nucleotide: SEQ ID NO: 50)

```
GAT GTT TTG ATG ACC CAA ACT CCA CTC TCC CTG CCT GTC AGT CTT      45
 D   V   L   M   T   Q   T   P   L   S   L   P   V   S   L

GGA GAT CAA GCC TCC ATC TCT TGC AGA TCT AGT CAG AGC CTT GTA      90
 G   D   Q   A   S   I   S   C   R   S   S   Q   S   L   V
                                 (SEQ ID NO: 38)

CAT ATT AAT GGA AAC ACC TAT TTA GAA TGG TAC CTG CAG AAA CCC     135
 H   I   N   G   N   T   Y   L   E   W   Y   L   Q   K   P
      CDR1

GGC CAG TCT CCA AAG CTC CTG ATC TAC AAA GTT TCC AAC CGA TTT     180
 G   Q   S   P   K   L   L   I   Y   K   V   S   N   R   F
                                    (SEQ ID NO: 39) CDR2

TCT GGG GTC CCT GAC AGG TTC AGT GGC AGT GGA TCA GGG ACA GAT     225
 S   G   V   P   D   R   F   S   G   S   G   S   G   T   D

TTC ACA CTC AAG ATC AGC AGA GTG GAG CCT GAG GAT CTG GGA GTT     270
 F   T   L   K   I   S   R   V   E   P   E   D   L   G   V

TAT TAC TGC TCT CAA GGT TCA CAT GTT CCG TGG ACG TTC GGT GGA     315
 Y   Y   C   S   Q   G   S   H   V   P   W   T   F   G   G
            (SEQ ID NO: 40) CDR3

GGC ACC AAG GTG GAA ATC AAA CGG
 G   T   K   V   E   I   K   R
```

| | 1E12 | 3F11 | 3E10 | 5E6 | 8H3 |
|---|---|---|---|---|---|
| EC50 | 1.474e-010 | 2.674e-010 | 2.241e-010 | 2.336e-010 | 8.110e-011 |

| Antibody clone ID | $K_a$ | $K_d$ | $K_D$ (M) |
|---|---|---|---|
| 1E12 | 1.460E+5 | 1.666E-5 | 1.141E-10 |
| 3F11 | 1.058E+5 | 1.893E-5 | 1.789E-10 |
| 3E10 | 1.935E+5 | 3.042E-6 | 1.572E-11 |
| 5E6 | 1.239E+4 | 4.802E-6 | 3.877E-10 |
| 8H3 | 3.987E+5 | 8.559E-5 | 2.147E-10 |

SEQUENCE LISTING

```
<160> NUMBER OF SEQ ID NOS: 51

<210> SEQ ID NO 1
<211> LENGTH: 118
<212> TYPE: PRT
<213> ORGANISM: Mus musculus

<400> SEQUENCE: 1

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ile Phe Ile Ser Phe
            20                  25                  30

Trp Ile His Trp Val Lys Gln Arg Pro Gly Gln Gly Leu Glu Trp Ile
        35                  40                  45

Gly Asn Ile Asp Pro Ser Asp Ser Glu Thr His Tyr Asn Glu Lys Phe
    50                  55                  60

Arg Asp Lys Ala Ser Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Leu Asp Gly Asp Tyr Gly Arg Ala Tyr Trp Gly Gln Gly Thr
            100                 105                 110

Leu Val Thr Val Ser Ala
        115

<210> SEQ ID NO 2
<211> LENGTH: 10
<212> TYPE: PRT
<213> ORGANISM: Mus musculus

<400> SEQUENCE: 2

Gly Tyr Ile Phe Ile Ser Phe Trp Ile His
1               5                   10

<210> SEQ ID NO 3
<211> LENGTH: 17
<212> TYPE: PRT
<213> ORGANISM: Mus musculus

<400> SEQUENCE: 3

Asn Ile Asp Pro Ser Asp Ser Glu Thr His Tyr Asn Gln Lys Phe Lys
1               5                   10                  15

Asp

<210> SEQ ID NO 4
<211> LENGTH: 11
<212> TYPE: PRT
<213> ORGANISM: Mus musculus
```

<400> SEQUENCE: 4

Ala Arg Leu Asp Gly Asp Tyr Gly Arg Ala Tyr
1               5                   10

<210> SEQ ID NO 5
<211> LENGTH: 118
<212> TYPE: PRT
<213> ORGANISM: Mus musculus

<400> SEQUENCE: 5

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ile Phe Ile Ser Phe
                20                  25                  30

Trp Ile His Trp Val Lys Gln Arg Pro Gly Gln Gly Leu Glu Trp Ile
            35                  40                  45

Gly Asn Ile Asp Pro Ser Asp Ser Glu Thr His Tyr Asn Glu Lys Phe
    50                  55                  60

Arg Asp Lys Ala Ser Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Leu Asp Gly Asp Tyr Gly Arg Ala Tyr Trp Gly Gln Gly Thr
                100                 105                 110

Leu Val Thr Val Ser Ala
        115

<210> SEQ ID NO 6
<211> LENGTH: 10
<212> TYPE: PRT
<213> ORGANISM: Mus musculus

<400> SEQUENCE: 6

Gly Tyr Ile Phe Ile Ser Phe Trp Ile His
1               5                   10

<210> SEQ ID NO 7
<211> LENGTH: 17
<212> TYPE: PRT
<213> ORGANISM: Mus musculus

<400> SEQUENCE: 7

Asn Ile Asp Pro Ser Asp Ser Glu Thr His Tyr Asn Glu Lys Phe Arg
1               5                   10                  15

Asp

<210> SEQ ID NO 8
<211> LENGTH: 11
<212> TYPE: PRT
<213> ORGANISM: Mus musculus

<400> SEQUENCE: 8

Ala Arg Leu Asp Gly Asp Tyr Gly Arg Ala Tyr
1               5                   10

<210> SEQ ID NO 9
<211> LENGTH: 117
<212> TYPE: PRT
<213> ORGANISM: Mus musculus

<400> SEQUENCE: 9

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Thr Ser
            20                  25                  30

Trp Ile Asn Trp Leu Lys Gln Arg Pro Gly Glu Gly Leu Glu Trp Leu
        35                  40                  45

Gly Arg Ile Tyr Pro Gly Asp Gly Asp Ile Asn Tyr Asn Gly Lys Phe
    50                  55                  60

Lys Asp Lys Ala Thr Leu Thr Ala Asp Lys Ser Ser Ser Thr Ala His
65                  70                  75                  80

Ile Gln Leu Asn Ser Leu Thr Ser Glu Asp Ser Ala Val Tyr Phe Cys
                85                  90                  95

Ala Arg Ser Asn His Tyr Tyr Phe Asp Phe Trp Gly Gln Gly Thr Thr
            100                 105                 110

Leu Thr Val Ser Ser
        115

<210> SEQ ID NO 10
<211> LENGTH: 10
<212> TYPE: PRT
<213> ORGANISM: Mus musculus

<400> SEQUENCE: 10

Gly Tyr Ala Phe Ser Thr Ser Trp Ile Asn
1               5                   10

<210> SEQ ID NO 11
<211> LENGTH: 17
<212> TYPE: PRT
<213> ORGANISM: Mus musculus

<400> SEQUENCE: 11

Arg Ile Tyr Pro Gly Asp Gly Asp Ile Asn Tyr Asn Gly Lys Phe Lys
1               5                   10                  15

Asp

<210> SEQ ID NO 12
<211> LENGTH: 8
<212> TYPE: PRT
<213> ORGANISM: Mus musculus

<400> SEQUENCE: 12

Ser Asn His Tyr Tyr Phe Asp Phe
1               5

<210> SEQ ID NO 13
<211> LENGTH: 117
<212> TYPE: PRT
<213> ORGANISM: Mus musculus

<400> SEQUENCE: 13

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Thr Ser
            20                  25                  30

Trp Met Asn Trp Val Lys Gln Arg Pro Gly Lys Gly Leu Glu Trp Ile
        35                  40                  45

```
Gly Arg Ile Tyr Pro Gly Asp Glu Asp Thr Asn Tyr Asn Gly Asn Phe
        50                  55                  60

Lys Gly Lys Ala Thr Leu Thr Ala Asp Lys Ser Ser Thr Ala Tyr
 65                  70                  75                  80

Met Gln Leu Ile Ser Leu Thr Ser Glu Asp Ser Ala Val Tyr Phe Cys
                     85                  90                  95

Ala Arg Ser Asp Asn Tyr Tyr Phe Asp Tyr Trp Gly Gln Gly Thr Thr
                100                 105                 110

Leu Thr Val Ser Ser
            115
```

<210> SEQ ID NO 14
<211> LENGTH: 10
<212> TYPE: PRT
<213> ORGANISM: Mus musculus

<400> SEQUENCE: 14

```
Gly Tyr Ala Phe Ser Thr Ser Trp Met Asn
 1               5                  10
```

<210> SEQ ID NO 15
<211> LENGTH: 17
<212> TYPE: PRT
<213> ORGANISM: Mus musculus

<400> SEQUENCE: 15

```
Arg Ile Tyr Pro Gly Asp Glu Asp Thr Asn Tyr Asn Gly Asn Phe Lys
 1               5                  10                  15

Gly
```

<210> SEQ ID NO 16
<211> LENGTH: 8
<212> TYPE: PRT
<213> ORGANISM: Mus musculus

<400> SEQUENCE: 16

```
Ser Asp Asn Tyr Tyr Phe Asp Tyr
 1               5
```

<210> SEQ ID NO 17
<211> LENGTH: 116
<212> TYPE: PRT
<213> ORGANISM: Mus musculus

<400> SEQUENCE: 17

```
Glu Val Gln Leu Val Glu Ser Gly Gly Gly Phe Val Lys Pro Gly Gly
 1               5                  10                  15

Ser Arg Lys Leu Ser Cys Ala Ala Ser Gly Phe Thr Phe Ser Asp Ser
                20                  25                  30

Gly Met His Trp Val Arg Gln Ala Pro Glu Lys Gly Leu Glu Trp Val
             35                  40                  45

Ala Tyr Ile Ser Ala Gly Ser Tyr Thr Ile Tyr Tyr Ala Asp Ile Val
        50                  55                  60

Lys Gly Arg Phe Thr Ile Ser Arg Asp Ser Ala Lys Asn Thr Leu Phe
 65                  70                  75                  80

Leu Gln Met Thr Ser Leu Arg Ser Glu Asp Thr Ala Ile Tyr Tyr Cys
                     85                  90                  95

Ala Arg Gly Asp Trp Tyr Phe Ala Val Trp Gly Ala Gly Thr Thr Val
                100                 105                 110
```

Thr Val Ser Ser
        115

<210> SEQ ID NO 18
<211> LENGTH: 10
<212> TYPE: PRT
<213> ORGANISM: Mus musculus

<400> SEQUENCE: 18

Gly Phe Thr Phe Ser Asp Ser Gly Met His
1               5                   10

<210> SEQ ID NO 19
<211> LENGTH: 17
<212> TYPE: PRT
<213> ORGANISM: Mus musculus

<400> SEQUENCE: 19

Tyr Ile Ser Ala Gly Ser Tyr Thr Ile Tyr Tyr Ala Asp Ile Val Lys
1               5                   10                  15

Gly

<210> SEQ ID NO 20
<211> LENGTH: 7
<212> TYPE: PRT
<213> ORGANISM: Mus musculus

<400> SEQUENCE: 20

Gly Asp Trp Tyr Phe Ala Val
1               5

<210> SEQ ID NO 21
<211> LENGTH: 112
<212> TYPE: PRT
<213> ORGANISM: Mus musculus

<400> SEQUENCE: 21

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Phe
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Thr Ala Thr Tyr Tyr Cys Gln Gln Asn Asn
                85                  90                  95

Glu Asp Pro Leu Thr Phe Gly Gly Gly Thr Lys Leu Glu Ile Lys Arg
            100                 105                 110

<210> SEQ ID NO 22
<211> LENGTH: 15
<212> TYPE: PRT
<213> ORGANISM: Mus musculus

<400> SEQUENCE: 22

Arg Ala Ser Glu Ser Val Asp Ser Phe Gly Asn Ser Phe Met His
1               5                   10                  15

<210> SEQ ID NO 23
<211> LENGTH: 7
<212> TYPE: PRT
<213> ORGANISM: Mus musculus

<400> SEQUENCE: 23

Leu Ala Ser Asn Leu Glu Ser
1               5

<210> SEQ ID NO 24
<211> LENGTH: 9
<212> TYPE: PRT
<213> ORGANISM: Mus musculus

<400> SEQUENCE: 24

Gln Gln Asn Asn Glu Asp Pro Leu Thr
1               5

<210> SEQ ID NO 25
<211> LENGTH: 112
<212> TYPE: PRT
<213> ORGANISM: Mus musculus

<400> SEQUENCE: 25

Asn Ile Ala Leu Thr Gln Ser Pro Thr Ser Leu Ala Val Ser Gln Gly
1               5                   10                  15

Gln Arg Ala Thr Ile Ser Cys Arg Ala Ser Glu Ser Val Asp Ser Asn
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Asp Asp Pro Trp Thr Phe Gly Gly Gly Thr Lys Leu Glu Ile Lys Arg
            100                 105                 110

<210> SEQ ID NO 26
<211> LENGTH: 15
<212> TYPE: PRT
<213> ORGANISM: Mus musculus

<400> SEQUENCE: 26

Arg Ala Ser Glu Ser Val Asp Ser Asn Gly Asn Ser Phe Met His
1               5                   10                  15

<210> SEQ ID NO 27
<211> LENGTH: 7
<212> TYPE: PRT
<213> ORGANISM: Mus musculus

<400> SEQUENCE: 27

Leu Ala Ser Asn Leu Glu Ser
1               5

<210> SEQ ID NO 28
<211> LENGTH: 9
<212> TYPE: PRT
<213> ORGANISM: Mus musculus

```
<400> SEQUENCE: 28

Gln Gln Asn Asn Asp Asp Pro Trp Thr
1               5

<210> SEQ ID NO 29
<211> LENGTH: 109
<212> TYPE: PRT
<213> ORGANISM: Mus musculus

<400> SEQUENCE: 29

Asp Val Gln Met Thr Gln Thr Thr Ser Ser Leu Ser Ala Ser Leu Gly
1               5                   10                  15

Asp Arg Val Thr Ile Asn Cys Arg Ala Ser Glu Asp Ile Arg Thr Tyr
            20                  25                  30

Leu Asn Trp Tyr Gln Gln Lys Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Asp Gln
65                  70                  75                  80

Glu Asp Ile Ala Thr Tyr Phe Cys Gln Gln Val His Thr Leu Pro Pro
                85                  90                  95

Trp Thr Phe Gly Gly Gly Thr Lys Leu Glu Ile Lys Arg
            100                 105

<210> SEQ ID NO 30
<211> LENGTH: 11
<212> TYPE: PRT
<213> ORGANISM: Mus musculus

<400> SEQUENCE: 30

Arg Ala Ser Glu Asp Ile Arg Thr Tyr Leu Asn
1               5                   10

<210> SEQ ID NO 31
<211> LENGTH: 7
<212> TYPE: PRT
<213> ORGANISM: Mus musculus

<400> SEQUENCE: 31

Tyr Thr Ser Arg Leu His Ser
1               5

<210> SEQ ID NO 32
<211> LENGTH: 10
<212> TYPE: PRT
<213> ORGANISM: Mus musculus

<400> SEQUENCE: 32

Gln Gln Val His Thr Leu Pro Pro Trp Thr
1               5                   10

<210> SEQ ID NO 33
<211> LENGTH: 89
<212> TYPE: PRT
<213> ORGANISM: Mus musculus

<400> SEQUENCE: 33

Ile Thr Cys Arg Ala Ser Asp Asp Ile Arg Thr Tyr Leu Asn Trp Tyr
1               5                   10                  15
```

```
Gln Gln Lys Pro Asp Gly Ser Val Lys Leu Leu Ile Tyr Tyr Thr Ser
            20                  25                  30

Arg Leu His Ser Gly Val Pro Ser Arg Phe Ser Gly Ser Gly Ser Gly
            35                  40                  45

Thr Asp Tyr Ser Leu Thr Ile Ser Asn Leu Val Gln Glu Asp Phe Ala
50                      55                  60

Thr Tyr Phe Cys Gln Gln Val His Thr Leu Pro Pro Trp Thr Phe Gly
65                  70                  75                  80

Gly Gly Thr Lys Leu Glu Ile Lys Arg
                85

<210> SEQ ID NO 34
<211> LENGTH: 11
<212> TYPE: PRT
<213> ORGANISM: Mus musculus

<400> SEQUENCE: 34

Arg Ala Ser Asp Asp Ile Arg Thr Tyr Leu Asn
1               5                   10

<210> SEQ ID NO 35
<211> LENGTH: 7
<212> TYPE: PRT
<213> ORGANISM: Mus musculus

<400> SEQUENCE: 35

Tyr Thr Ser Arg Leu His Ser
1               5

<210> SEQ ID NO 36
<211> LENGTH: 10
<212> TYPE: PRT
<213> ORGANISM: Mus musculus

<400> SEQUENCE: 36

Gln Gln Val His Thr Leu Pro Pro Trp Thr
1               5                   10

<210> SEQ ID NO 37
<211> LENGTH: 113
<212> TYPE: PRT
<213> ORGANISM: Mus musculus

<400> SEQUENCE: 37

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ile
            20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Pro Glu Asp Leu Gly Val Tyr Tyr Cys Ser Gln Gly
                85                  90                  95

Ser His Val Pro Trp Thr Phe Gly Gly Gly Thr Lys Val Glu Ile Lys
            100                 105                 110

Arg
```

<210> SEQ ID NO 38
<211> LENGTH: 16
<212> TYPE: PRT
<213> ORGANISM: Mus musculus

<400> SEQUENCE: 38

Arg Ser Ser Gln Ser Leu Val His Ile Asn Gly Asn Thr Tyr Leu Glu
1               5                   10                  15

<210> SEQ ID NO 39
<211> LENGTH: 7
<212> TYPE: PRT
<213> ORGANISM: Mus musculus

<400> SEQUENCE: 39

Lys Val Ser Asn Arg Phe Ser
1               5

<210> SEQ ID NO 40
<211> LENGTH: 9
<212> TYPE: PRT
<213> ORGANISM: Mus musculus

<400> SEQUENCE: 40

Ser Gln Gly Ser His Val Pro Trp Thr
1               5

<210> SEQ ID NO 41
<211> LENGTH: 354
<212> TYPE: DNA
<213> ORGANISM: Mus musculus

<400> SEQUENCE: 41
caggtccaac tgcagcagcc ggggactgag ctggtgaagc ctggggcttc agtgaaactg      60
tcctgtaagg cttctggcta catcttcatc agcttctgga tacactgggt gaagcagagg     120
cctggacaag gccttaaatg gattggtaat attgaccctt ctgatagtga aactcactac     180
aatcaaaagt tcaaggacaa ggccacattg actgtagaca atcctccag cacagcctac      240 atgcagctca gcagcctgac atctgaggac tctgcggtct attactgtgc aagattggat     300
ggtgactacg ggagggctta ctggggccaa gggactctgg tcactgtctc tgca           354

<210> SEQ ID NO 42
<211> LENGTH: 354
<212> TYPE: DNA
<213> ORGANISM: Mus musculus

<400> SEQUENCE: 42
caggtccaac tgcagcagcc tggggctgaa ctggtgaagc ctggggcttc agtgaaactg      60
tcctgcaagg cttctggcta catcttcatc agcttctgga tacactgggt gaagcagagg     120
cctggacaag gccttgaatg gattggtaat attgaccctt ctgatagtga aactcactac     180
aatgaaaaat tcaggacaa ggcctcattg actgtagaca agtcctccag cacagcctac      240
atgcagctca gcagcctgac atctgaggac tctgcggtct atttctgtgc aaggttggat     300
ggtgactacg ggagggctta ctggggccaa gggactctgg tcactgtctc tgca           354

<210> SEQ ID NO 43
<211> LENGTH: 351
<212> TYPE: DNA
<213> ORGANISM: Mus musculus

<400> SEQUENCE: 43

```
caggttcagt tgcagcagtc tggacctgag ctggtgaagc ctggggcctc agtgaagatt      60
tcctgcaagg cctctggcta tgcattcagt acctcctgga taaactggct gaagcagagg     120
cctggagagg gtcttgagtg gcttggacgg atttatcctg agatggaga tataaactac      180
aatgggaagt tcaaggacaa ggccacactg actgcagaca atcctccag tacagcccac      240
atacaactca acagcctgac atctgaggac tctgcggtct acttctgtgc aagatcgaat    300
cattactact ttgacttctg gggccaaggc accactctca cagtctcctc a              351
```

<210> SEQ ID NO 44
<211> LENGTH: 351
<212> TYPE: DNA
<213> ORGANISM: Mus musculus

<400> SEQUENCE: 44

```
caggttcagc tgcagcagtc tggacctgag ctggtgaagc ctggggcctc agtgaagatt      60
tcctgcaagg cttctggcta tgcattcagt acctcctgga tgaactgggt aaagcagagg    120
cctggaaagg gtcttgagta gattggacgg atttatcctg agatgaaga tactaactac      180
aatgggaact tcaagggcaa ggccacactg actgcagaca atcttccag tacagcctat      240
atgcaactca tcagcctgac atctgaggac tctgcggtct acttctgtgc aagatcggat    300
aattactact ttgactactg gggccaaggc accactctca cagtctcctc a              351
```

<210> SEQ ID NO 45
<211> LENGTH: 348
<212> TYPE: DNA
<213> ORGANISM: Mus musculus

<400> SEQUENCE: 45

```
gaggtgcagc tggtggagtc tgggggaggc tttgtgaagc tggagggtc ccggaaactc      60
tcctgtgcag cctctggatt cactttcagt gactctggaa tgcactgggt ccgtcaggct    120
ccagagaagg ggctggagtg ggttgcatac attagtgctg gcagttatac catctactat    180
gcagacatag tgaagggccg attcaccatc tctagagaca gtgccaagaa cacctgttc     240
ctgcaaatga ccagtctaag gtctgaggac acagccattt attattgtgc aagaggggac    300
tggtacttcg ctgtctgggg cgcagggacc acggtcaccg tctcctca                 348
```

<210> SEQ ID NO 46
<211> LENGTH: 336
<212> TYPE: DNA
<213> ORGANISM: Mus musculus

<400> SEQUENCE: 46

```
aacattgtgc tgacccaatc tccagcttct ttggctgtgt ctctaggaca gagggccacc     60
atatcctgca gagccagtga aagtgttgat agttttggca atagtttat gcactggtac    120
cagcagaaac caggacagcc gcccaaactc ctcatctatc ttgcatccaa cctagaatct    180
ggggtccctg ccaggttcag tggcagtggg tctaggacag acttcaccct caccattgat    240
cctgtggagg ctgatgatac tgcaacctat tactgtcagc aaaataatga ggatccgttg    300
acgttcggtg gaggcaccaa actggaaatc aaacgg                              336
```

<210> SEQ ID NO 47
<211> LENGTH: 336
<212> TYPE: DNA

<213> ORGANISM: Mus musculus

<400> SEQUENCE: 47

```
aacattgcgc tgacccaatc tccaacttct ttggctgtgt ctcaagggca gagggccacc      60
atatcctgca gagccagtga aagtgttgat agtaatggca atagttttat gcactggtac     120
cagcagaaac caggacagcc acccaaactc ctcatctatc ttgcatccaa cctagaatct     180
ggggtccctg ccaggttcag tggcagtggg tctaggacag atttcaccct caccattgat     240
cctgtggagg ctgatgatgc tgcaacctat tactgtcagc aaaataatga cgatccgtgg     300
acgttcggtg aggcacaaa gctggaaatc aaacgg                                336
```

<210> SEQ ID NO 48
<211> LENGTH: 327
<212> TYPE: DNA
<213> ORGANISM: Mus musculus

<400> SEQUENCE: 48

```
gatgtccaga tgacacagac tacatcctcc ctgtctgcct ctctgggaga cagagtcacc      60
atcaattgca gggcaagtga agacattaga acttatttaa actggtatca gcagaaacca     120
gatggaacta ttaaactcct gatctactac acatccagat tacattcagg agtcccatca     180
aggttcagtg gcagtgggtc tggaacagat tattctctca ccattagcaa cctggaccaa     240
gaagatattg ccacttactt ttgtcaacag gttcatacac ttcctccgtg gacgttcggt     300
ggaggcacca aactggaaat caaacgg                                         327
```

<210> SEQ ID NO 49
<211> LENGTH: 327
<212> TYPE: DNA
<213> ORGANISM: Mus musculus

<400> SEQUENCE: 49

```
gatatccaga tgacacagac tacatcctcc ctgtctgcct ctctgggaga cagagtcacc      60
atcacttgca gggcaagtga tgacattagg acttatttaa actggtatca gcagaaacca     120
gatggatctg ttaaactcct gatctactac acatcaagat tacactcggg agtcccatca     180
aggttcagtg gcagtgggtc tggaacagat tattctctca ccattagcaa cctggttcaa     240
gaagattttg ccacttattt ttgccaacag gttcatacgc ttcctccgtg gacgttcggt     300
ggaggcacca agctggaaat caaacgt                                         327
```

<210> SEQ ID NO 50
<211> LENGTH: 339
<212> TYPE: DNA
<213> ORGANISM: Mus musculus

<400> SEQUENCE: 50

```
gatgttttga tgacccaaac tccactctcc ctgcctgtca gtcttggaga tcaagcctcc      60
atctcttgca gatctagtca gagccttgta catattaatg gaaacaccta tttagaatgg     120
tacctgcaga aacccggcca gtctccaaag ctcctgatct acaaagtttc caaccgattt     180
tctggggtcc ctgacaggtt cagtggcagt ggatcaggga cagatttcac actcaagatc     240
agcagagtgg agcctgagga tctgggagtt tattactgct ctcaaggttc acatgttccg     300
tggacgttcg gtggaggcac caaggtggaa atcaaacgg                            339
```

<210> SEQ ID NO 51
<211> LENGTH: 310

```
<212> TYPE: PRT
<213> ORGANISM: Homo sapiens

<400> SEQUENCE: 51

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu His Pro Asp Leu Ala Ala Leu Ile Val Tyr Trp Glu Met Glu
        50                  55                  60

Asp Lys Asn Ile Ile Gln Phe Val His Gly Glu Glu Asp Leu Lys Val
65                  70                  75                  80

Gln His Ser Ser Tyr Arg Gln Arg Ala Arg Leu Leu Lys Asp Gln Leu
                85                  90                  95

Ser Leu Gly Asn Ala Ala Leu Gln His Pro Asp Leu Ile Thr Asp Val
            100                 105                 110

Lys Leu Gln Asp Ala Gly Val Tyr Arg Cys Met Ile Ser Tyr Gly Gly
        115                 120                 125

Ala Asp Tyr Lys Arg Ile Thr Val Lys Val Asn Ala Pro Tyr Asn Lys
    130                 135                 140

Ile Asn Gln Arg Ile Leu Val Val Asp Pro Val Thr Ser Glu His Pro
145                 150                 155                 160

Asp Leu His Glu Leu Thr Cys Gln Ala Glu Gly Tyr Pro Lys Ala Glu
                165                 170                 175

Val Ile Trp Thr Ser Ser Asp His Gln Val Leu Ser Gly Lys Thr Thr
            180                 185                 190

Thr Thr Asn Ser Lys Arg Glu Glu Lys Leu Phe Asn Val Thr Ser Thr
        195                 200                 205

Leu Arg Ile Asn His Pro Asp Leu Thr Thr Thr Asn Glu Ile Phe Tyr
    210                 215                 220

Cys Thr Phe Arg Arg Leu Asp Pro Glu Glu Asn His Thr Ala Glu Leu
225                 230                 235                 240

Val Ile Pro Glu Leu Pro Leu Ala His Pro Pro Asn Glu Arg Thr His
                245                 250                 255

Leu Val Ile Leu Gly Ala Ile Leu Leu Cys His Pro Asp Leu Leu Gly
            260                 265                 270

Val Ala Leu Thr Phe Ile Phe Arg Leu Arg Lys Gly Arg Met Met Asp
        275                 280                 285

Val Lys Lys Cys Gly Ile Gln Asp Thr Asn Ser Lys Lys Gln Ser Asp
    290                 295                 300

Thr His Leu Glu Glu Thr
305                 310
```

ANTI-HUMAN PD-L1 ANTIBODIES AND THEIR USES

FIELD OF THE INVENTION

The present invention relates to novel human sequence monoclonal antibodies, particularly to human monoclonal antibodies that specifically bind to PD-L1 with high affinities. In particular, the invention relates to the uses of such molecules in the treatment and diagnosis of human diseases.

BACKGROUND OF THE INVENTION

The protein Programmed Death 1 (PD-1) is an inhibitory member of the CD28 family of receptors, which also include CD28, CTLA-4, ICOS, and BTLA. PD-1 is expressed on activated B cells, T cells, and myeloid cells (Bennett, Luxenberg et al. 2003). Its ligand, programmed cell death-ligand 1 (PD-L1), is expressed on some tumor cells and by activated B cells and T cells, dendritic cells, macrophages, and fibroblasts cells (Hansen, Du Pasquier et al. 2009). PD-L1 binds PD-1 to attenuate cellular immune responses by inducing T-cell apoptosis or exhaustion. Blockade of the PD-1/PD-L1 pathway with monoclonal antibodies (against PD-1 or PD-L1) is a promising therapeutic approach that is being explored in studies of many types of human cancers (Sanmamed and Chen 2014). The results of these studies suggest that PD-L1 plays an important role in helping tumors to escape immune systems by facilitating PD-1/PD-L1 pathway activation.

PD-L1 expression has been observed in various solid tumors, including breast cancer (Qin, Zeng et al. 2015), lung cancer (Ameratunga, Asadi et al. 2016), gastric cancer (Wu, Zhu et al. 2006), colorectal cancer (Rosenbaum, Bledsoe et al. 2016), hepatocellular carcinoma (Kan and Dong 2015), renal cell carcinoma (Shin, Jeon et al. 2016), testicular cancer (Cierna, Mego et al. 2016) and papillary thyroid cancer (Chowdhury, Veyhl et al. 2016). Moreover, several meta-analyses have shown that PD-L1 overexpression signifies a poor prognosis in many cancer types (Wang, Wang et al. 2015, Xu, Xu et al. 2015, Zhang, Kang et al. 2015, Iacovelli, Nole et al. 2016). Therefore, there is a need for better antibodies against PD-L1 for the treatment or diagnosis of diseases or conditions mediated by PD-L1.

SUMMARY OF THE INVENTION

In one aspect, the present invention relates to antibodies that specifically bind to human PD-L1. An antibody of the invention comprises a heavy-chain variable region comprising three heavy-chain complementarity-determining regions, HCDR1, HCDR2, and HCDR3, with the sequences of SEQ ID NOs: 2-4, or 6-8, or 10-12, or 14-16, or 18-20, and a light-chain variable region comprising three light-chain complementarity-determining regions, LCDR1, LCDR2, and LCDR3, with the sequences of SEQ ID NOs: 22-24, or 26-28, or 30-32, or 34-36, or 38-40.

In some embodiments, the HCDR1 sequence is GYIFISFWIH (SEQ ID NO: 2), the HCDR2 sequence is NIDPSDSETHYNQKFKD (SEQ ID NO:3), the HCDR3 sequence is LDGDYGRAY (SEQ ID NO:4); or the HCDR1 sequence is GYIFISFWIH (SEQ ID NO: 6), the HCDR2 sequence is NIDPSDSETHYNEKFRD (SEQ ID NO: 7), the HCDR3 sequence is LDGDYGRAY (SEQ ID NO: 8); or the HCDR1 sequence is GYAFSTSWIN (SEQ ID NO: 10), the HCDR2 sequence is RIYPGDGDINYNGKFKD (SEQ ID NO: 11), the HCDR3 sequence is SNHYYFDF (SEQ ID NO: 12); or the HCDR1 sequence is GYAFSTSWMN (SEQ ID NO: 14), the HCDR2 sequence is RIYPGDEDTNYNGNFKG (SEQ ID NO: 15), the HCDR3 sequence is SDNYYFDY (SEQ ID NO: 16); or the HCDR1 sequence is GFTFSDSGMH (SEQ ID NO: 18), the HCDR2 sequence is YISAGSYTIYYADIVKG (SEQ ID NO: 19), the HCDR3 sequence is GDWYFAV (SEQ ID NO: 20); wherein the HCDR sequences are defined according to the method of Chothia.

In accordance with embodiments of the invention, a heavy chain variable region sequence of a human anti-PD-L1 antibody has the sequence of SEQ ID NO: 1, 5, 9, 13, or 17 shown in FIGS. 1A-1E.

In another aspect, the present application relates to antibodies that specifically bind human PD-L1, comprising a light chain variable region having LCDR1, LCDR2 and LCDR3 sequences, wherein: the LCDR1 sequence is RASESVDSFGNSFMH (SEQ ID NO: 22), the LCDR2 sequence is LASNLES (SEQ ID NO: 23), the LCDR3 sequence is QQNNEDPLT (SEQ ID NO: 24), or the LCDR1 sequence is RASESVDSNGNSFMH (SEQ ID NO: 26), the LCDR2 sequence is LASNLES (SEQ ID NO: 27), the LCDR3 sequence is QQNNDDPWT (SEQ ID NO: 28); or the LCDR1 sequence is RASEDIRTYLN (SEQ ID NO: 30), the LCDR2 sequence is YTSRLHS (SEQ ID NO: 31), the LCDR3 sequence is QQVHTLPPWT (SEQ ID NO: 32); or the LCDR1 sequence is RASDDIRTYLN (SEQ ID NO: 34), the LCDR2 sequence is YTSRLHS (SEQ ID NO: 35), the LCDR3 sequence is QQVHTLPPWT (SEQ ID NO: 36); or the LCDR1 sequence is RSSQSLVHINGNTYLE (SEQ ID NO: 38), the LCDR2 sequence is KVSNRFS (SEQ ID NO: 39), the LCDR3 sequence is SQGSHVPWT (SEQ ID NO: 40); wherein the LCDR sequences are defined according to method of Chothia.

In accordance with some embodiments of the invention, a light-chain variable region of an antibody that specifically binds human PD-L1 has the sequence of SEQ ID NO: 21, 25, 29, 33, or 37, shown in FIGS. 2A-2E.

In another aspect, the present invention relates to an antibody that specifically binds human PD-L1, comprising a heavy chain variable region having HCDR1, HCDR2, and HCDR3 and a light chain variable region having LCDR1, LCDR2 and LCDR3, wherein the HCDR1 sequence is GYIFISFWIH (SEQ ID NO: 2), the HCDR2 sequence is NIDPSDSETHYNQKFKD (SEQ ID NO:3), the HCDR3 sequence is LDGDYGRAY (SEQ ID NO:4); or the HCDR1 sequence is GYIFISFWIH (SEQ ID NO: 6), the HCDR2 sequence is NIDPSDSETHYNEKFRD (SEQ ID NO: 7), the HCDR3 sequence is LDGDYGRAY (SEQ ID NO: 8); or the HCDR1 sequence is GYAFSTSWIN (SEQ ID NO: 10), the HCDR2 sequence is RIYPGDGDINYNGKFKD (SEQ ID NO: 11), the HCDR3 sequence is SNHYYFDF (SEQ ID NO: 12); or the HCDR1 sequence is GYAFSTSWMN (SEQ ID NO: 14), the HCDR2 sequence is RIYPGDEDTNYNGNFKG (SEQ ID NO: 15), the HCDR3 sequence is SDNYYFDY (SEQ ID NO: 16); or the HCDR1 sequence is GFTFSDSGMH (SEQ ID NO: 18), the HCDR2 sequence is YISAGSYTIYYADIVKG (SEQ ID NO: 19), the HCDR3 sequence is GDWYFAV (SEQ ID NO: 20), LCDR1 sequence is RASESVDSFGNSFMH (SEQ ID NO: 22), the LCDR2 sequence is LASNLES (SEQ ID NO: 23), the LCDR3 sequence is QQNNEDPLT (SEQ ID NO: 24), or the LCDR1 sequence is RASESVDSNGNSFMH (SEQ ID NO: 26), the LCDR2 sequence is LASNLES (SEQ ID NO: 27), the LCDR3 sequence is QQNNDDPWT (SEQ ID NO: 28); or the LCDR1 sequence is RASEDIRTYLN (SEQ ID NO: 30), the LCDR2 sequence is YTSRLHS (SEQ ID NO: 31), the LCDR3 sequence is QQVHTLPPWT (SEQ ID NO: 32);

or the LCDR1 sequence is RASDDIRTYLN (SEQ ID NO: 34), the LCDR2 sequence is YTSRLHS (SEQ ID NO: 35), the LCDR3 sequence is QQVHTLPPWT (SEQ ID NO: 36); or the LCDR1 sequence is RSSQSLVHINGNTYLE (SEQ ID NO: 38), the LCDR2 sequence is KVSNRFS (SEQ ID NO: 39), the LCDR3 sequence is SQGSHVPWT (SEQ ID NO: 40); and wherein the HCDR and LCDR sequences are defined according to the method of Chothia.

In some embodiments, a heavy-chain variable region sequence of an antibody that specifically binds human PD-L1 has the sequence of SEQ ID NO: 1, 5, 9, 13, or 17, and a light-chain variable region sequence of the antibody that specifically binds human PD-L1 has the sequence of SEQ ID NO: 21, 25, 29, 33, or 37.

In some embodiments, a heavy-chain variable region sequence of an antibody that specifically binds human PD-L1 has the sequence of SEQ ID NO: 1, and a light-chain variable region sequence of the antibody that specifically binds human PD-L1 has the sequence of SEQ ID NO: 21.

In some embodiments, a heavy-chain variable region sequence of an antibody that specifically binds human PD-L1 has the sequence of SEQ ID NO: 5, a light-chain variable region sequence of the antibody that specifically binds human PD-L1 has the sequence of SEQ ID NO: 25.

In some embodiments, a heavy-chain variable region sequence of an antibody that specifically binds human PD-L1 has the sequence of SEQ ID NO: 9, and a light-chain variable region sequence of an antibody that specifically binds human PD-L1 has the sequence of SEQ ID NO: 29.

In some embodiments, a heavy-chain variable region sequence of an antibody that specifically binds human PD-L1 has the sequence of SEQ ID NO: 13, and a light-chain variable region sequence of an antibody that specifically binds human PD-L1 has the sequence of SEQ ID NO: 33.

In some embodiments, a heavy-chain variable region sequence of an antibody that specifically binds human PD-L1 has the sequence of SEQ ID NO: 17, and a light-chain variable region sequence of an antibody that specifically binds human PD-L1 has the sequence of SEQ ID NO: 37.

In some embodiments of the invention, an antibody that specifically binds human PD-L1 is a full antibody, an Fab fragment, an F(ab')2 fragment, or an ScFv fragment.

In some embodiments, an antibody that specifically binds human PD-L1 is a fully human antibody.

In some embodiments, an antibody that specifically binds human PD-L1 comprises a heavy chain constant region selected from IgG1, IgG2, or IgG4 isoforms and a light chain constant region selected from κ subtype or λ isoform.

In some embodiments, an antibody (or a binding fragment thereof) of the invention forms part of a bispecific or multi-specific antibody by conjugating with another specific binding domain for a second target. The other specific binding domain for the second target, for example, may be anti-CD3, anti-ICOS or anti-TIM3, etc. In some embodiments, an antibody (or a binding fragment thereof) of the invention forms part of an antibody-drug conjugate (ADC) by conjugating with a drug (payload). The drug or payload may be selected for its ability to modulate a function in the PD-L1-expressing cells or PD-1-expression cells. Such drugs or payloads, for example, may include DM1, MMAE or MMAF.

Another aspect of the present invention relates to a pharmaceutical composition for use in treating and/or preventing a disease associated with PD-1 and/or PD-L1 signaling, wherein the pharmaceutical composition comprises the above-described antibody, or a binding fragment thereof, that binds specifically to the human PD-L1. The PD-L1 mediated disease may be a cancer. The cancers may include, but are not limited to: melanoma, non-small cell lung cancer, renal cancer, breast cancer, leukemia, cancer and other advanced solid tumors.

BRIEF DESCRIPTION OF DRAWINGS

FIGS. 1A-1E show composite, human heavy chain (FIG. 1A, 1E12; FIG. 1B, 3F11; FIG. 1C, 3E10; and FIG. 1D, 8H3; FIG. 1E, 5E6) variable region sequences designed to correspond to that of the mouse anti-human PD-L1 antibody.

FIGS. 2A-2E show composite, human light chain (FIG. 2A, 1E12; FIG. 2B, 3F11; FIG. 2C, 3E10; FIG. 2D, 8H3; FIG. 2E, 5E6) variable region sequences designed to correspond to that of the mouse anti-human PD-1 antibody.

FIG. 3A shows bindings of human anti-PD-L1 to PD-L1 using ELISA. FIG. 3B shows results of human anti-PD-L1 to PD-L1 using BIACORE® 2000 (GE Healthcare).

FIG. 4A shows antibodies 1E12 and 3F11; FIG. 4B shows antibodies 3E10, 8H3 and 5E6.

FIG. 6 show the anti-PDL-1 antibodies binding to HCC827 cells assayed with Flow Cytometry.

DETAILED DESCRIPTION OF THE INVENTION

Figures 3A, 3B:
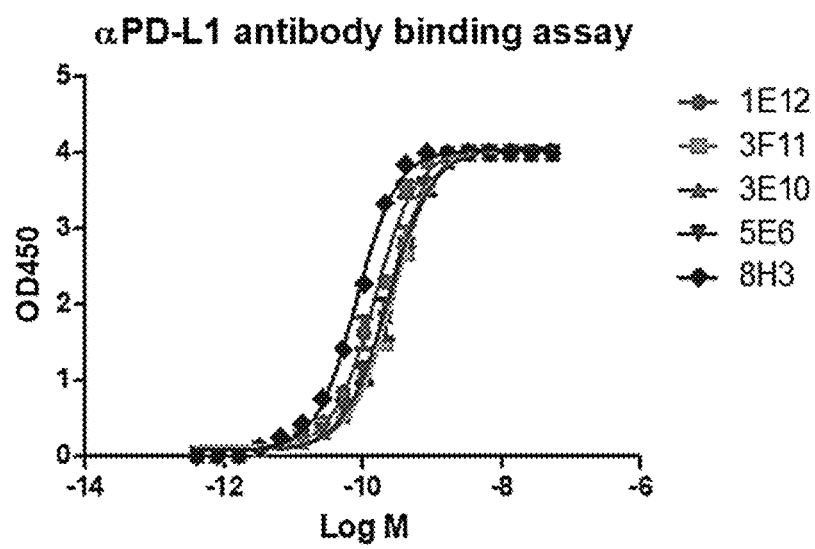
FIGS. 3A-3B illustrate the bindings of various antibodies to PD-L1.

The present invention relates to novel antibodies that bind specifically to and have high affinities for PD-L1 and can deliver therapeutic benefits to a subject. The antibodies of the invention, which may be human or humanized, can be used as therapeutics for treating and/or diagnosing a variety of disorders mediated by PD-L1, which are more fully described herein.

Particularly, an antibody, or an antigen-binding fragment thereof, according to embodiments of the invention specifically binds to an epitope in human PD-L1 or a fragment thereof, wherein the human PD-L1 has the amino acid sequence of SEQ ID NO: 51, and the epitope comprises: the Lysine residue at position 178, and the threonine residue at position 179.

An antibody according to embodiments of the invention can be full-length (for example, an IgG1 or IgG4 antibody), or may comprise only an antigen-binding portion (for example, a Fab, F(ab')2, or scFv fragment), and may be modified to affect functionalities as needed.

An antibody or antigen-binding fragment thereof according to embodiments of the invention specifically binds to human PD-L1. PD-L1, also known as CD274 or B7 homolog 1, is a 40 kDa type 1 transmembrane protein that has been speculated to play a major role in suppressing the immune system during particular events, such as pregnancy, tissue allografts, autoimmune disease and other disease states such as hepatitis. Normally, the immune system reacts to foreign antigens that are associated with exogenous or endogenous danger signals, which trigger a proliferation of antigen-specific CD8+ T cells and/or CD4+ helper cells. The binding of PD-L1 to PD-1 or B7.1 transmits an inhibitory signal that reduces the proliferation of these T cells and can also induce apoptosis, which is further mediated by a lower regulation of the gene Bcl-2.

The term "antibody" has its ordinary meaning and comprises two heavy (H) chains and two light (L) chains inter-connected by disulfide bonds. Each heavy chain comprises a heavy chain variable region (abbreviated herein as HCVR or VH) comprising three CDRs (HCDR1, HCDR2, and HCDR3) and four framework regions (FRs). Each light chain comprises a light chain variable region (abbreviated herein as LCVR or VL) comprising three CDRs (LCDR1, LCDR2, and LCDR3) and four FRs. In different embodiments of the invention, the FRs of the anti-PD-L1 antibody (or antigen-binding portion thereof) may be identical to the human germline sequences, or may be naturally or artificially modified. An amino acid consensus sequence may be defined based on a side-by-side analysis of two or more CDRs.

The term "antigen-binding fragment" of an antibody as used herein includes any fragment of an antibody that can specifically bind an antigen to form a complex. Non-limiting examples of an antigen-binding fragment includes: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody typically comprises at least one variable domain. The variable domain may be of any size or amino acid composition and will generally comprise at least one CDR, which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

As with a full antibody molecule, an antigen-binding fragment may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

Antibodies of the invention may be used as antibody-drug conjugates (ADCs), which can specifically target PD-L1. The conjugates on the ADCs may modulate the immune cells that express PD-L1 or cells that interact with cells that express PD-L1 (e.g., PD-1 expressing cells). These ADCs can use any antibody of the invention, or an antigen-binding fragment thereof. The drugs (payloads) that are conjugated to the antibody (or binding fragment) can be any that are commonly used in ADCs. The methods for conjugation can be those known in the art.

As applied to polypeptides, the term "substantial similarity" or "substantially similar" means that two peptide sequences, when optimally aligned, such as by the programs GAP or BESTFIT using default gap weights or by BLAST, share at least 95% sequence identity, even more preferably at least 98% or 99% sequence identity. According to embodiments of the invention, the Gap and Best fit program in GCG software was used with default parameters to determine sequence homology or sequence identity between closely related polypeptides.

In embodiments of the invention, an anti-PD-L1 antibody, or an antigen-binding fragment thereof, comprises a heavy chain variable region and a light chain variable region, wherein the heavy chain variable region comprises 3 CDR regions, CDRH1 (or HCDR1), CDRH2 (or HCDR2) and CDRH3 (or HCDR3) regions, and the light chain variable region comprises 3 CDR regions, CDRL1 (or LCDR1), CDRL2 (or LCDR2) and CDRL3 (or LCDR3) regions.

As used herein, the term "a disease mediated by PD-1 or PD-L1" refers to a disease associated with PD-1/PD-L1 signaling leading to immune suppression or exhaustion. Such diseases include those associated with autoimmunity, neurological disorders, stroke, and cancer. (N. Kuol et al., Immunotherapy, 2018, 10(2): 149-160). As used herein, "treating" refers to alleviation of symptoms of a disease or condition; it does not have to be complete cure.

Referring to FIGS. 1A-1E and 2A-2E, in some embodiments of the invention, the CDRH1 region comprises the amino acid sequence of SEQ ID NO: 2, the CDRH2 region comprises the amino acid sequence of SEQ ID NO: 3, the CDRH3 region comprises the amino acid sequence of SEQ ID NO: 4, the CDRL1 region comprises the amino acid sequence of SEQ ID NO: 22, the CDRL2 region comprises the amino acid sequence of SEQ ID NO: 23, and the CDRL3 region comprises the amino acid sequence of SEQ ID NO: 24.

In some embodiments of the invention, the CDRH1 region comprises the amino acid sequence of SEQ ID NO: 6, the CDRH2 region comprises the amino acid sequence of SEQ ID NO: 7, the CDRH3 region comprises the amino acid sequence of SEQ ID NO: 8, the CDRL1 region comprises the amino acid sequence of SEQ ID NO: 26, the CDRL2 region comprises the amino acid sequence of SEQ ID NO: 27, and the CDRL3 region comprises the amino acid sequence of SEQ ID NO: 28.

In some embodiments of the invention, the CDRH1 region comprises the amino acid sequence of SEQ ID NO: 10, the CDRH2 region comprises the amino acid sequence of SEQ ID NO: 11, the CDRH3 region comprises the amino acid sequence of SEQ ID NO: 12, the CDRL1 region comprises the amino acid sequence of SEQ ID NO: 30, the CDRL2 region comprises the amino acid sequence of SEQ ID NO: 31, and the CDRL3 region comprises the amino acid sequence of SEQ ID NO: 32.

In some embodiments of the invention, the CDRH1 region comprises the amino acid sequence of SEQ ID NO: 14, the CDRH2 region comprises the amino acid sequence of SEQ ID NO: 15, the CDRH3 region comprises the amino acid sequence of SEQ ID NO: 16, the CDRL1 region comprises the amino acid sequence of SEQ ID NO: 34, the CDRL2 region comprises the amino acid sequence of SEQ ID NO: 35, and the CDRL3 region comprises the amino acid sequence of SEQ ID NO: 36.

In some embodiments of the invention, the CDRH1 region comprises the amino acid sequence of SEQ ID NO: 18, the CDRH2 region comprises the amino acid sequence of SEQ ID NO: 19, the CDRH3 region comprises the amino acid sequence of SEQ ID NO: 20, the CDRL1 region comprises the amino acid sequence of SEQ ID NO: 38, the CDRL2 region comprises the amino acid sequence of SEQ ID NO: 39, and the CDRL3 region comprises the amino acid sequence of SEQ ID NO: 40.

In some embodiments of the invention, an anti-PD-L1 antibody, or an antigen-binding fragment thereof, comprises a heavy chain variable region comprising the amino acid sequence of SEQ ID NO: 1 and a light chain variable region comprising the amino acid sequence of SEQ ID NO: 21. Preferably, the heavy chain variable region is encoded by the nucleic acid sequence of SEQ ID NO: 41, and the light chain variable region is encoded by the nucleic acid sequence of SEQ ID NO: 46.

In some embodiments of the invention, an anti-PD-L1 antibody, or an antigen-binding fragment thereof, comprises a heavy chain variable region comprising the amino acid sequence of SEQ ID NO: 5 and a light chain variable region comprising the amino acid sequence of SEQ ID NO: 25. Preferably, the heavy chain variable region is encoded by the nucleic acid sequence of SEQ ID NO: 45, and the light chain variable region is encoded by the nucleic acid sequence of SEQ ID NO: 47.

In some embodiments of the invention, an anti-PD-L1 antibody, or an antigen-binding fragment thereof, comprises a heavy chain variable region comprising the amino acid sequence of SEQ ID NO: 9 and a light chain variable region comprising the amino acid sequence of SEQ ID NO: 29. Preferably, the heavy chain variable region is encoded by the nucleic acid sequence of SEQ ID NO: 49, and the light chain variable region is encoded by the nucleic acid sequence of SEQ ID NO: 48.

In some embodiments of the invention, an anti-PD-L1 antibody, or an antigen-binding fragment thereof, comprises a heavy chain variable region comprising the amino acid sequence of SEQ ID NO: 13 and a light chain variable region comprising the amino acid sequence of SEQ ID NO: 33. Preferably, the heavy chain variable region is encoded by the nucleic acid sequence of SEQ ID NO: 44, and the light chain variable region is encoded by the nucleic acid sequence of SEQ ID NO: 43.

In some embodiments of the invention, an anti-PD-L1 antibody, or an antigen-binding fragment thereof, comprises a heavy chain variable region comprising the amino acid sequence of SEQ ID NO: 17 and a light chain variable region comprising the amino acid sequence of SEQ ID NO: 37. Preferably, the heavy chain variable region is encoded by the nucleic acid sequence of SEQ ID NO: 42, and the light chain variable region is encoded by the nucleic acid sequence of SEQ ID NO: 50.

Antibodies of the invention were confirmed to have specific bindings with PD-L1 via ELISA. Briefly, PD-L1 was coated on a 96-well ELISA plate (0.1 µg/well). After binding of anti-PD-L1 antibodies, a goat anti mouse IgG conjugated with horse radish peroxidase (HRP) was used as a second antibody and 3,3',5,5'-Tetramethylbenzidine (TMB) was used as a substrate to assess the antibody-PD-L1 bindings. The OD405 was read to calculate the activities.

As shown in FIG. 3A, several mouse hybridoma anti-human PD-L1 antibodies (mAbs 1E12, 3F11, 8H3, 3E10, and 5E6) all show specific and tight bindings with PD-L1. FIG. 3B shows the binding parameters and affinities of these antibodies as determined by BIACORE® T200 (GE Healthcare). Briefly, a CM5 BIACORE® chip was coated with human PD-L1 on the active channel. The active channels were injected with mouse hybridoma anti-human PD-L1 antibodies (mAbs 1E12, 3F11, 8H3, 3E10, and 5E6) or its variants sequentially at various concentrations, and a channel injected with buffer alone was used as a blank control. The affinities were determined with the method of single-cycle kinetics. The data was fitted with a 1:1 binding model using BIACORE® T200 evaluation software to obtain the kinetics constants ($K_a$: association constant; $K_d$: dissociation constant; $K_D=K_d/K_a$).

That antibodies of the invention can bind human PD-L1 tightly and specifically suggests that these antibodies should be able to interfere with the binding between PD-1 and PD-L1. The abilities of various antibodies of the invention to block the binding of PD-L1 to PD-1 were confirmed using ELISA. Briefly, 100 ng/well PD-L1-Fc was coated on a 96-well plate. Then, 5 ug/well PD-1-biotin and different concentrations of anti-human PD-L1 antibodies were added. The binding was allowed to proceed at 37° C. for 1 hour. After washing with PBS, HRP-Conjugated Streptavidin was added, followed by addition of 1 MB (3,3',5,5'-tetramethylbenzidine). The amounts of biotinated PD-1 binding to the PD-L1-Fc were quantified with OD405 readings.

Figure 4A:
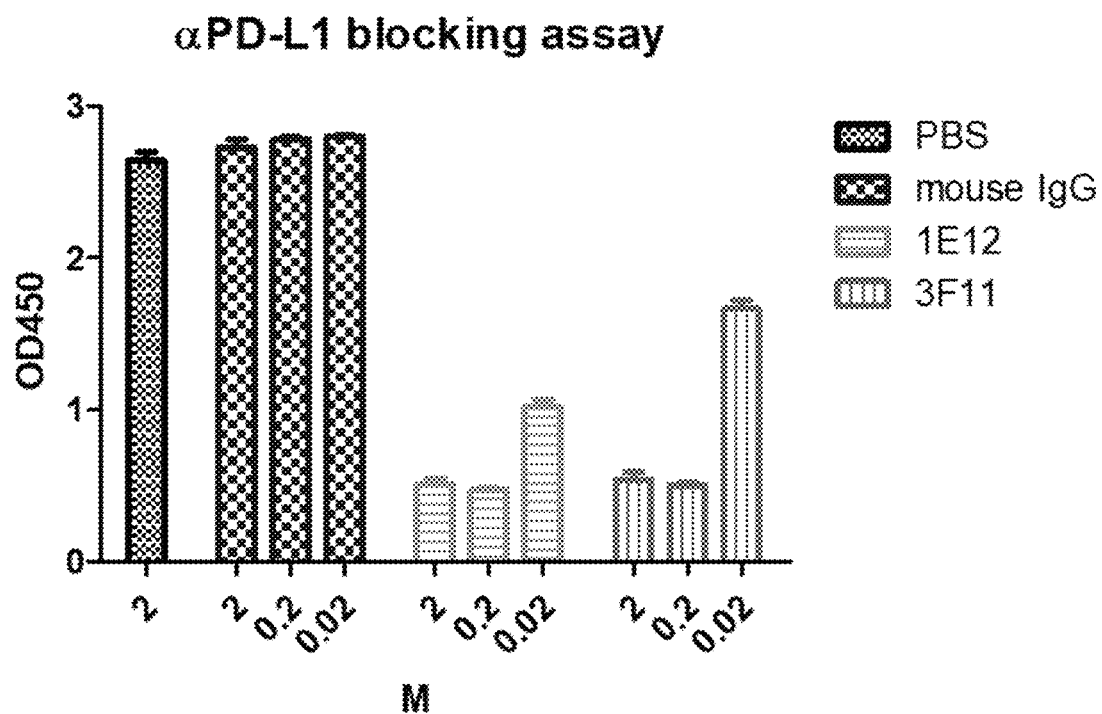
FIGS. 4A-4B illustrate the ability of the various antibodies to block binding of PD-L1 to PD-1.
Figure 4B:
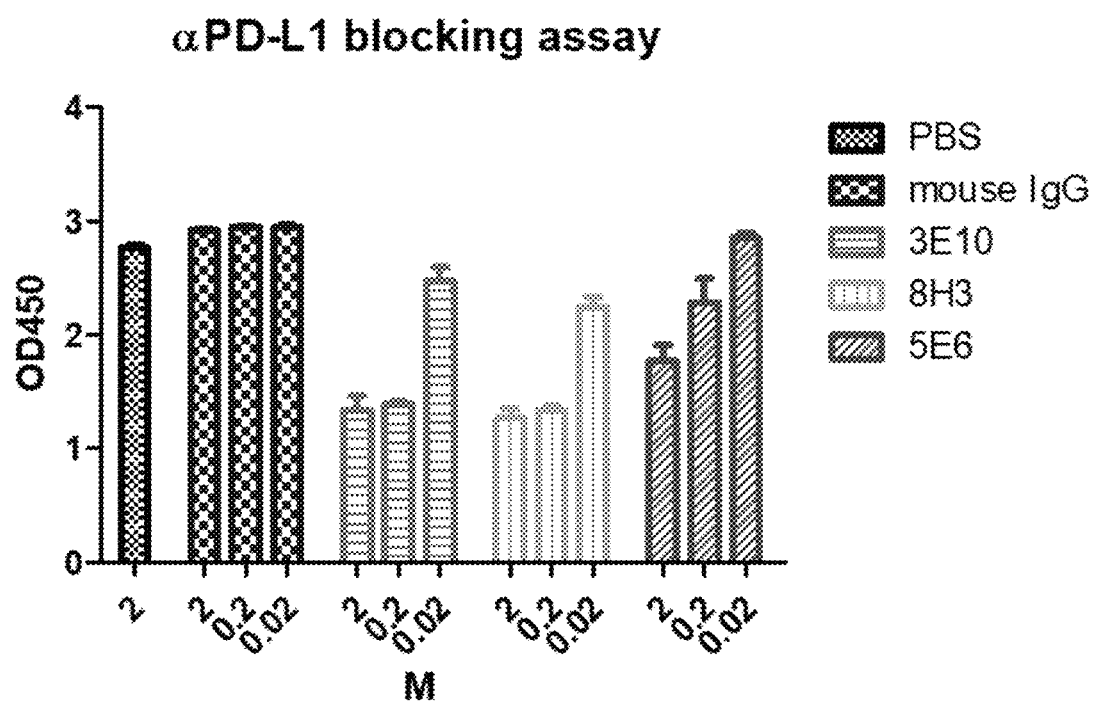

As shown in FIG. 4A, mAbs of the invention (e.g., 1E12 and 3F11) effectively blocked the bindings between PD-1 and PD-L1, while the control mouse IgG did not. Similarly, FIG. 4B shows that mAbs 3E10, 8H3, and 5E6 could interfere with the interactions between PD-1 and PD-L1, while the control mouse IgG could not.

While the above experiment tests the binding of antibodies of the invention to PD-L1 molecule in vitro, such binding was also tested with PD-1 and PD-L1 respectively expressed on interaction cells. For example, the PD-1/PD-L1 blockage assay may use any commercial kit, such as the kit from Promega (Maddison, WI, USA). The Promega PD-1/PD-L1 Blockade Bioassay is a bioluminescent cell-based assay. The assay kit consists of two genetically engineered cell lines: PD-1 Effector Cells, which are Jurkat T cells expressing human PD-1 and a luciferase reporter driven by an NFAT response element (NFAT-RE), and PD-L1 aAPC/CHO-K1 Cells, which are CHO-K1 cells expressing human PD-L1 and an engineered cell surface protein designed to activate cognate TCRs in an antigen-independent in inner.

When the two cell types are co-cultured, the PD-1/PD-L1 interaction inhibits TCR signaling and NFAT-RE-mediated luminescence. Addition of anti-PD-L1 antibodies of the invention that block the PD-1/PD-L1 interactions can release the inhibitory signal, leading to TCR activation and NFAT-RE-mediated luminescence. The bioluminescent signal can be detected and quantified using the Bio-Glo™ Luciferase Assay System and a standard luminometer, such as the GloMax™ Discover System from Promega (Maddison, WI, USA).

Figure 5:
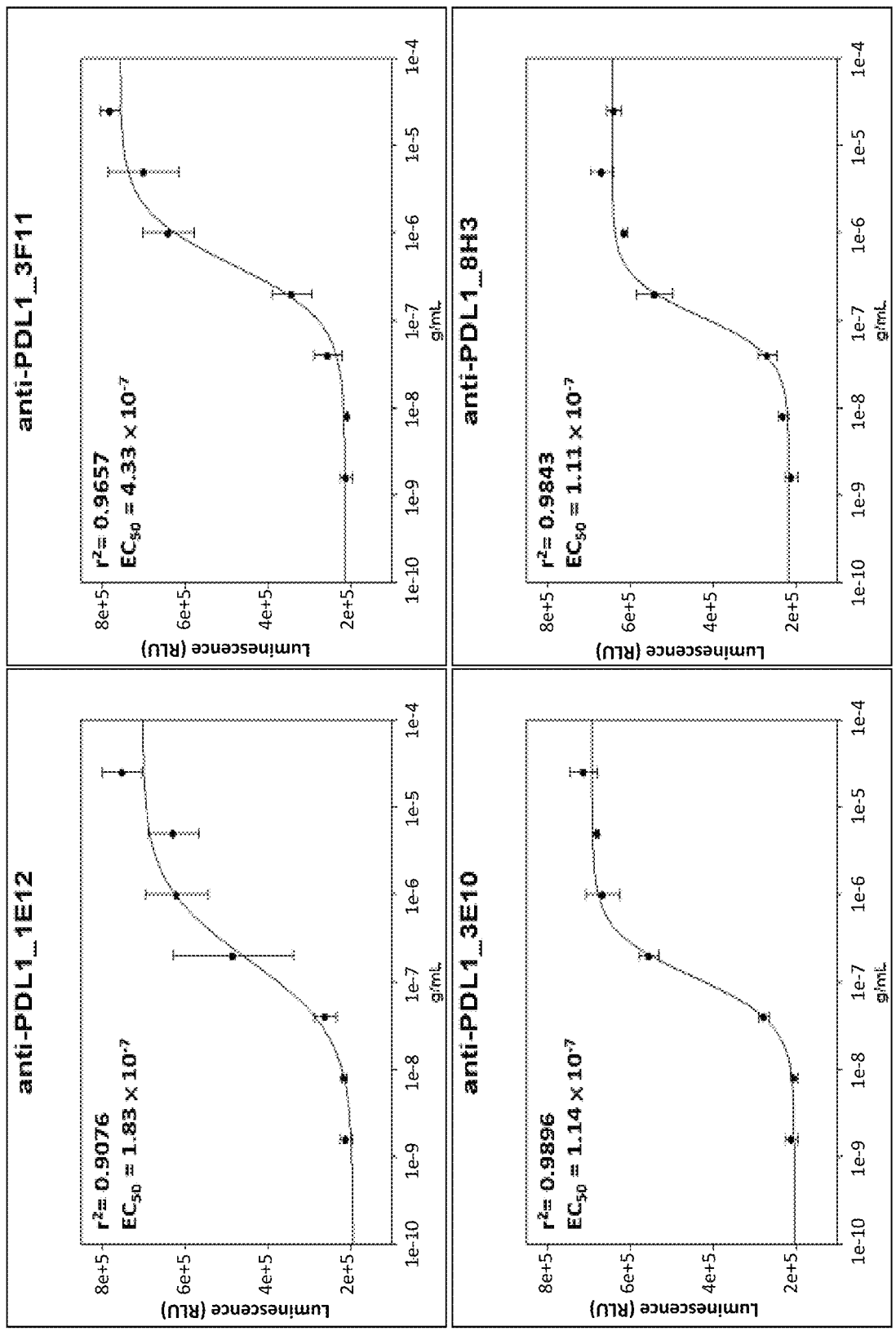
FIG. 5 illustrate the ability of the various antibodies to induce PD-1/PD-L1 blockade.

As shown in FIG. 5, mAbs of the invention 1E12, 3F11, 3E10, and 8H3 all show specific and potent activities that block PD-1/PD-L1 interactions. Other antibodies of the invention also show similar activities. These results confirm that antibodies of the invention would be effective in relieving immune suppression mediated by PD-1 and PD-L1 interactions on interacting cells. Therefore, antibodies of the invention should be useful as therapeutics for diseases arising from immune suppression or exhaustion due to PD-1 and/or PD-L1 signaling. Such diseases include various cancers.

Figure 6:
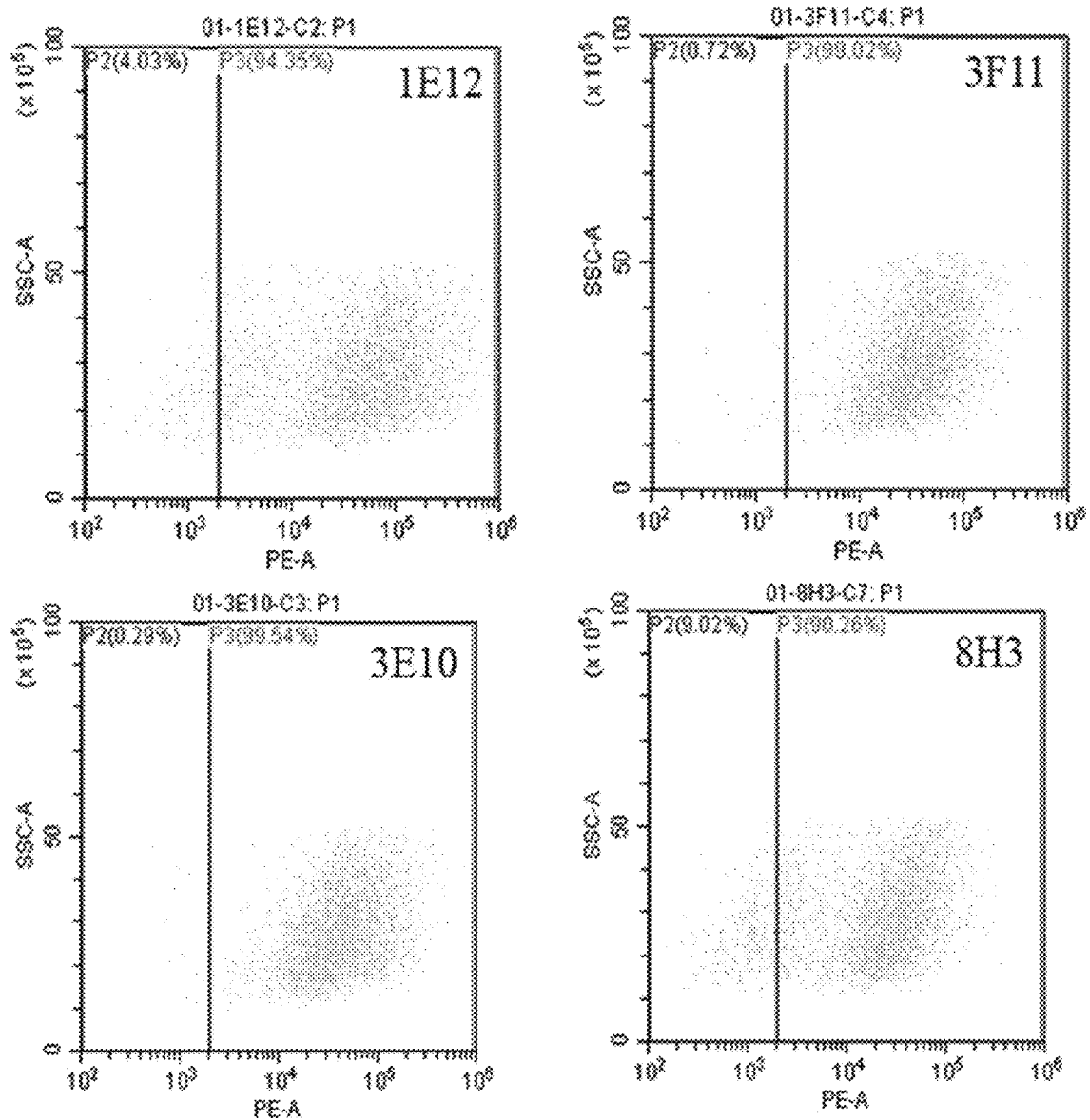

To further validate the utility of antibodies of the invention in cancer treatments, the abilities of these antibodies to bind PD-L1 expressed on cancer cells were assessed. For example, binding of anti-PD-L1 antibodies to PD-L1 expressing cells was assayed by Flow Cytometry using HCC827 cells (lung adenocarcinoma), which express high-level PD-L1. Briefly, HCC827 cells (PD-L1 high) were incubated with anti-PD-L1 antibodies for 1 hour, then analyzed using flow cytometry. As shown in FIG. 6, mAbs of the invention 1E12, 3E10, 3F11, and 8H3 all can bind HCC827 cells, indicating that these antibodies can recognize PD-L1 on the cancer cell surfaces. Other antibodies of the invention also show similar activities. Therefore, antibodies of the invention can be used to treat cancers by binding to PD-L1 expressed on cancer cells and thereby inhibiting PD-L1 mediated immune suppression or exhaustion.

In addition to blockade of PD-1/PD-L1 interactions, antibodies binding to PD-L1 may also trigger receptor internalization/recycling. Receptor internalization or recycling would also make PD-L1 unavailable for interactions with PD-1. Thus, the abilities of anti-PDL-1 antibodies of the invention to trigger PD-L1 internalization were investigated. Briefly, to explore these blocking/recycling processes of PD-L1, MDA-MB-231 cells (an epithelial, human breast cancer cell line) were treated with 1 µg/mL anti-PD-L1 antibodies at 4° C. and 37° C. and monitored over 24 hours. Then, at various time points, the cells were analyzed with Flow Cytometry.

Figure 7A:
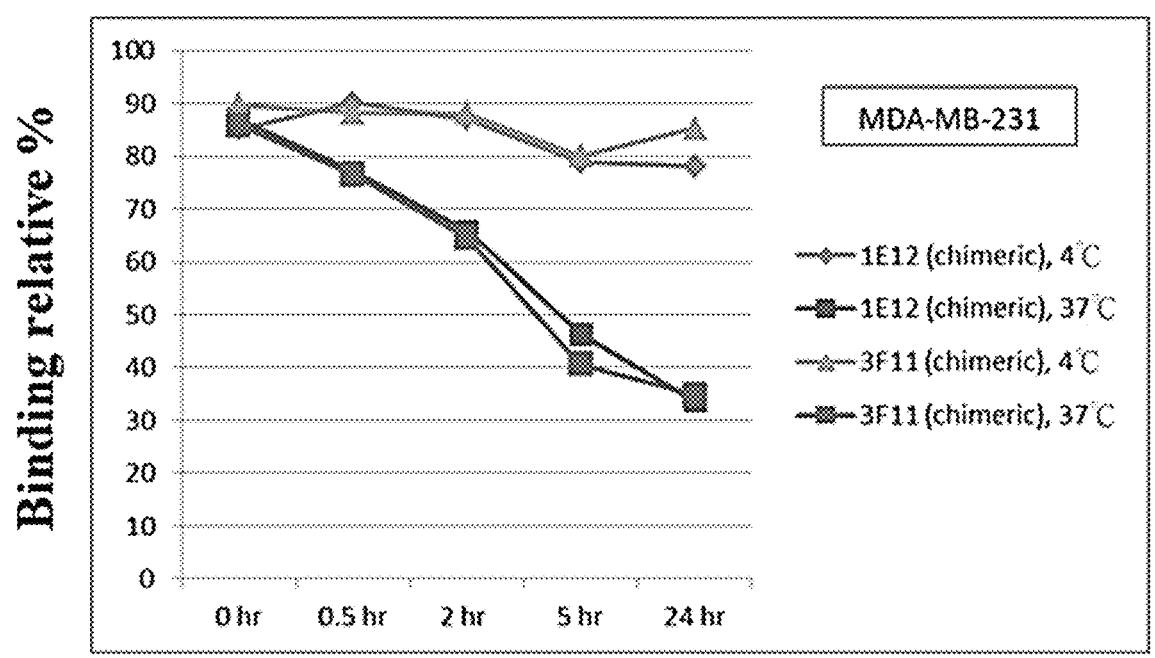
FIGS. 7A and 7B shows the anti-PDL-1 antibodies binding and internalization assay in MDA-MB-231 cells using Flow Cytometry.
Figure 7B:
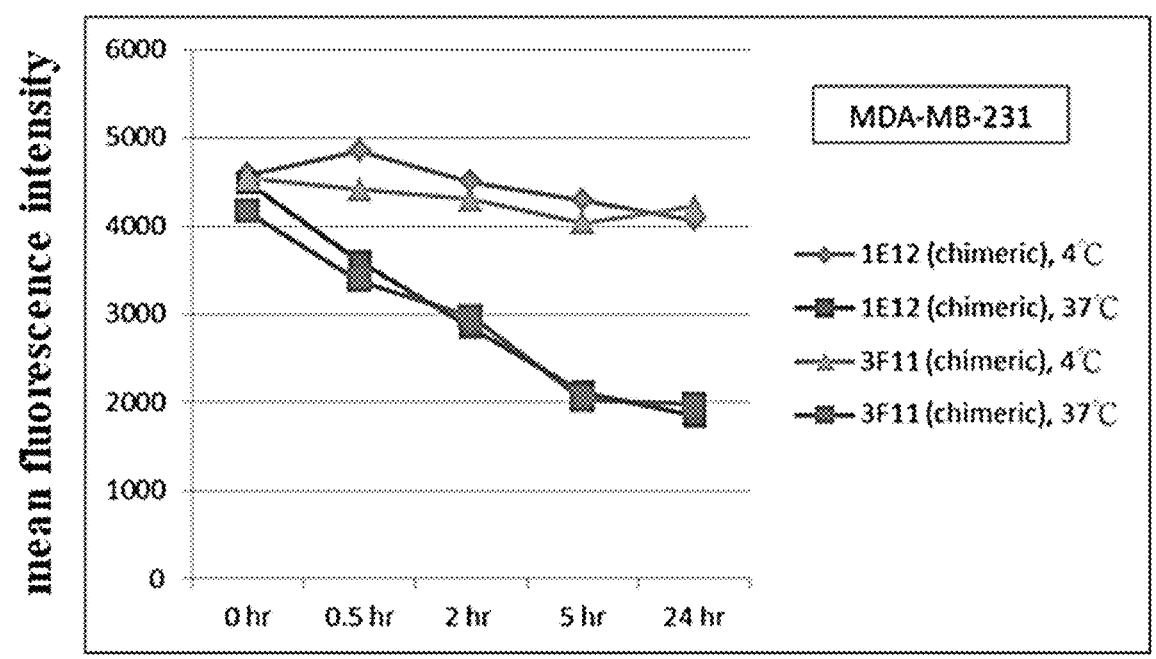

As shown in FIGS. 7A and 7B, mAbs 1E12 and 3F11 could bind to MDA-MB-231 cells and became internalized. The internalization occurred at 37° C., but not at 4° C., in a time-dependent manner. These results indicate that antibodies of the invention can block PD-1/PD-L1 interactions by binding to PD-L1, as well as triggering internalization of PD-L1. Internalization makes PD-L1 unavailable and would be more effective (than simple blinding) in blocking PD-L1 mediated signaling pathway. Therefore, antibodies of the invention should be more effective in the treatment of cancers or diseases that are mediated by PD-L1.

Figure 8:
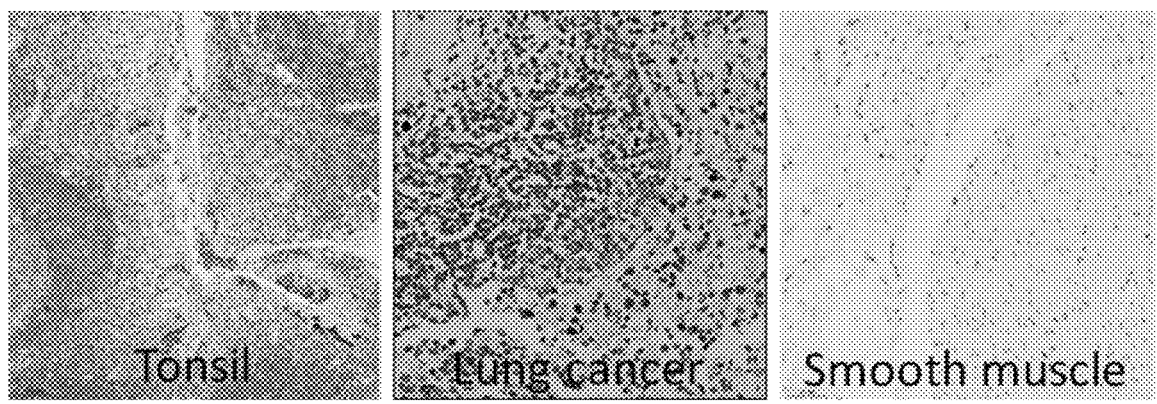
FIG. 8 shows the anti-PD-L1 antibody 3F11 immunohistochemistry in human tissue specimens.

Because anti-PD-L1 antibodies of the invention can bind PD-L1 specifically and tightly, it would be also useful for detection of PD-L1, which is highly expressed in several cancer cells. As shown in FIG. 8, anti-PD-L1 antibody 3F11 immunohistochemistry staining of human tissue specimens revealed only weak staining in normal tissues (e.g., tonsil and smooth muscle), whereas the staining of lung cancer tissue is very strong. These results indicate that anti-PD-L1 antibodies of the invention are useful for detection of cells or tissue that express PD-L1, such as cancer cells. Therefore, these antibodies should be useful as diagnostic agents for the detection of cancers and for prognosis/monitoring of cancers during and/or after treatments.

The above examples clearly show that anti-PD-L1 antibodies of the invention can bind human PD-L1 specifically and tightly. These antibodies can also interfere with the interactions between PD-1 and PD-L1 and block the PD-1/PD-L1 bindings. In addition, these antibodies can cause internalization of PD-L1, rendering PD-L1 unavailable for binding with PD-1. As a result, antibodies of the invention should be effective therapeutics for treating diseases mediated by PD-1/PD-L1 interactions. Such diseases include, for example, cancers. Examples of cancers include, but are not limited to, lung cancer, breast cancer, prostate cancer, colorectal cancer, etc. In addition, antibodies of the invention may be used as reagents to detect PD-L1, which is useful in the diagnosis of PD-L1 expression or in the prognosis during treatments.

Some embodiments of the invention relate to methods for treating, or alleviating conditions/symptoms of, a disease mediated by PD-1 and/or PD-L1 signaling; such diseases may include cancers. To demonstrate the utility of antibodies of the invention in treating cancers, a murine syngeneic model was used. Briefly, MC38 cells (colon adenocarcinoma cells) were injected subcutaneously into C57BL/6 mice on day 0. On days 6, 9, and 13, the mice were treated with antibodies (e.g., 1E12, 3F11, 3E10, and 8H3) of the invention at 5 mpk (mg/kg) each time. An IgG (not anti-PD-L1) was used as a control. The tumor growths in various treatment groups were monitored until day 16.

Figure 9:
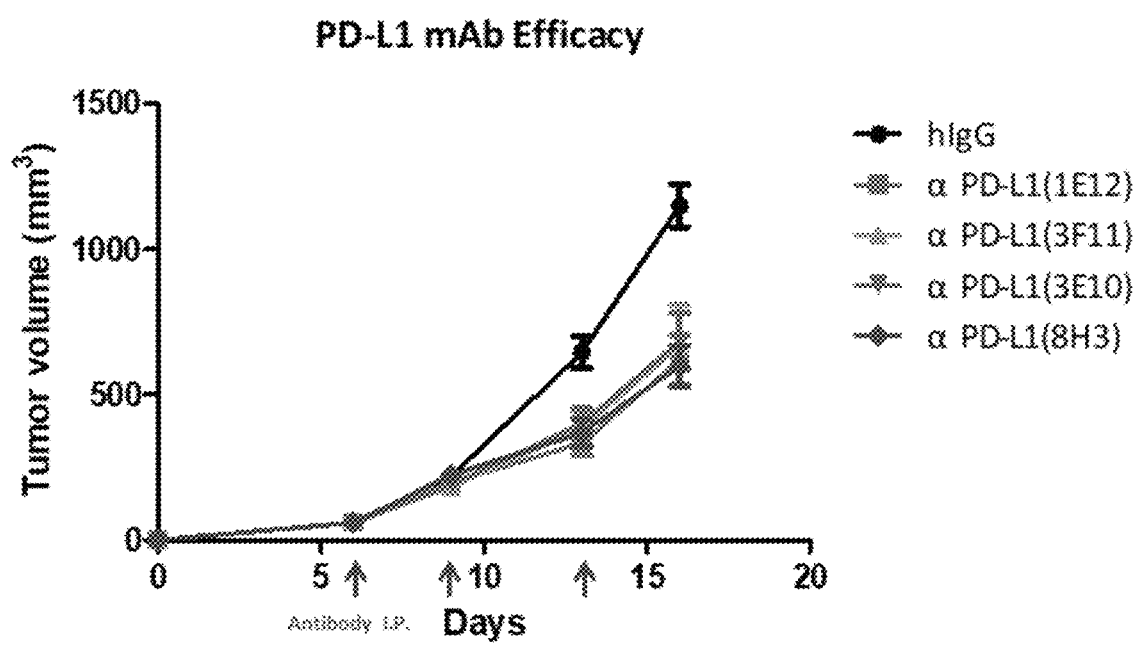
FIG. 9 shows the in vivo efficacy of anti-PD-L1 mAb treatment in the murine syngeneic MC38 colon cancer model.

As shown in FIG. 9, anti-PD-L1 mAbs of the invention (e.g., 1E12, 3F11, 3E10, and 8H3) were effective in suppressing tumor growths in this in vivo colorectal cancer model. Other antibodies of the invention also have similar effects. These results clearly demonstrate that antibodies of the invention will be useful for clinical uses to treat cancers, such as lung cancer, breast cancer, prostate cancer, colorectal cancer, etc.

In addition, antibodies of the invention are highly specific for human PD-L1. they recognize unique epitopes with high specificities and affinities. These properties would make them more useful as therapeutics. Indeed, in a mouse xenograft model of MDA-MB231 breast cancer cells, antibody of the invention (3F11 and 1E12) homed in the tumor over time, i.e., the binding intensity increases with time up to 120 hours. In contrast, an FDA approved antibody, Atezolizumab, did not have sufficient binding avidity and appeared to be distributed throughout the animal. As a result, Atezolizumab was cleared by the system relatively fast and did not show much binding by 120 hours. Because the antibodies of the invention bind to the cancer cells tightly, very little of the antibodies appears in circulation to be cleared by the system. As a result, antibodies of the invention have much longer in vivo half-lives. Therefore, antibodies of the invention can be used in smaller doses and with less frequent administrations, substantially reducing the treatment costs and minimizing any potential adverse effects.

As compared to the prior art anti-PD-L1 antibodies, antibodies of the invention have more favorable pharmacokinetic properties (e.g., higher avidities and longer half-lives), which are likely due to binding to different epitopes on human PD-L1. Epitope mappings indicate that antibodies of the invention bind to human PD-L1 at epitopes located in the regions involving residues 171-180 and 206-210. These epitope regions are different from those of known antibodies. For example, critical residues involved in the bindings of prior art antibodies (e.g., atezolizumab and durvalumab) to PD-L1 involves E58 and R125 on PD-L1. (Lee et al., "Molecular mechanism of PD-1/PD-L1 blockade via anti-PD-L1 antibodies atezolizumab and durvalumab," Scientific Reports, (2017), 7: 5532).

Further analysis of the epitopes for bindings of antibodies of the invention using alanine scanning revealed that residues 178 and 179 are particularly important for the bindings, as shown in the following Table:

| mAb | Wild-Type PD-L1 | Amino-Acid Substitution Mutation | | | | | | | |
|---|---|---|---|---|---|---|---|---|---|
| | | 57-66 | 104-111 | 123-130 | 171-180 | 178 | 179 | 178&179 | 206-210 |
| 1E12 | O | O | O | O | — | — | — | — | — |
| 3F11 | O | O | O | O | — | — | — | — | — |
| 8H3 | O | O | O | O | — | — | O | — | — |
| 3E10 | O | O | O | O | — | — | O | — | — |
| 5E6 | O | O | O | O | — | O | O | O | — |

O: no effect on binding
—: effect on binding

In sum, antibodies of the invention can bind PD-L1 specifically and tightly, including PD-L1 on cell surfaces. The PD-L1 expressing cells include cancer cells, such as lung cancer cells, colorectal cancer cells (e.g., MC38 cells), breast cancer cells (e.g., MDA-MB-231 cells), etc. These antibodies can interfere with the binding between PD-1 and PD-L1, leading to blockade of PD-1 and/or D-L1 signaling pathways. In addition, binding by antibodies of the invention also causes internalization of PD-L1, rendering it unavailable for interaction with PD-1. As a result, antibodies of the invention can alleviate or reverse immune suppression or exhaustion caused by PD-1 and/or D-L1 signaling. Therefore, antibodies of the invention are useful therapeutic agents for treating or alleviating conditions of diseases associated with immune suppression or exhaustion caused by PD-1 and PD-L1 interactions.

Bindings of PD-L1 by antibodies of the invention involve hereto unknown epitopes on human PD-L1, and bindings to these new epitope result in unexpected high specificity and avidities, leading to more favorable pharmacokinetic properties (e.g., more focused binding on tumor cells, less free antibodies in circulation, and longer half-lives). As a result, antibodies of the invention can be used at lower doses and with less frequent administration, thereby reducing the costs and side effects and increasing patient compliance.

While embodiments of the invention have been illustrated with a limited number of examples, one skilled in the art would appreciate that other modifications and variations are possible. Therefore, the scope of protection of the invention should only be limited by the attached claims.

REFERENCES

1. Ameratunga, M., K. Asadi, X. Lin, M. Walkiewicz, C. Murone, S. Knight, P. Mitchell, P. Boutros and T. John (2016). "PD-L1 and Tumor Infiltrating Lymphocytes as Prognostic Markers in Resected NSCLC." *PLoS One* 11(4): e0153954.
2. Bennett, F., D. Luxenberg, V. Ling, I. M. Wang, K. Marquette, D. Lowe, N. Khan, G. Veldman, K. A. Jacobs, V. E. Valge-Archer, M. Collins and B. M. Carreno (2003). "Program death-1 engagement upon TCR activation has distinct effects on costimulation and cytokine-driven proliferation: attenuation of ICOS, IL-4, and IL-21, but not CD28, IL-7, and IL-15 responses." *J Immunol* 170(2): 711-718.
3. Chowdhury, S., J. Veyhl, F. Jessa, O. Polyakova, A. Alenzi, C. MacMillan, R. Ralhan and P. G. Walfish (2016). "Programmed death-ligand 1 overexpression is a prognostic marker for aggressive papillary thyroid cancer and its variants." *Oncotarget* 7(22): 32318-32328.
4. Cierna, Z., M. Mego, V. Miskovska, K. Machalekova, M. Chovanec, D. Svetlovska, K. Hainova, K. Rejlekova, D. Macak, S. Spanik, D. Ondrus, K. Kajo, J. Mardiak and P. Babal (2016). "Prognostic value of programmed-death-1 receptor (PD-1) and its ligand 1 (PD-L1) in testicular germ cell tumors." *Ann Oncol* 27(2): 300-305.
5. Hansen, J. D., L. Du Pasquier, M. P. Lefranc, V Lopez, A. Benmansour and P. Boudinot (2009). "The B7 family of immunoregulatory receptors: a comparative and evolutionary perspective." *Mol Immunol* 46(3): 457-472.
6. Iacovelli, R., F. Nole, E. Verri, G. Renne, C. Paglino, M. Santoni, M. Cossu Rocca, P. Giglione, G. Aurilio, D. Cullura, S. Cascinu and C. Porta (2016). "Prognostic Role of PD-L1 Expression in Renal Cell Carcinoma. A Systematic Review and Meta-Analysis." *Target Oncol* 11(2): 143-148.
7. Kan, G. and W. Dong (2015). "The expression of PD-L1 APE1 and P53 in hepatocellular carcinoma and its relationship to clinical pathology." *Eur Rev Med Pharmacol Sci* 19(16): 3063-3071.
8. Qin, T., Y D. Zeng, G. Qin, F. Xu, J. B. Lu, W. F. Fang, C. Xue, J. H. Zhan, X. K. Zhang, Q. F. Zheng, R. J. Peng, Z. Y Yuan, L. Zhang and S. S. Wang (2015). "High PD-L1 expression was associated with poor prognosis in 870 Chinese patients with breast cancer." *Oncotarget* 6(32): 33972-33981.
9. Rosenbaum, M. W., J. R. Bledsoe, V. Morales-Oyarvide, T. G. Huynh and M. Mino-Kenudson (2016). "PD-L1 expression in colorectal cancer is associated with microsatellite instability, BRAF mutation, medullary morphology and cytotoxic tumor-infiltrating lymphocytes." *Mod Pathol* 29(9): 1104-1112.
10. Sanmamed, M. F. and L. Chen (2014). "Inducible expression of B7-H1 (PD-L1) and its selective role in tumor site immune modulation." *Cancer J* 20(4): 256-261.
11. Shin, S. J., Y. K. Jeon, P. J. Kim, Y M. Cho, J. Koh, D. H. Chung and H. Go (2016). "Clinicopathologic Analysis of PD-L1 and PD-L2 Expression in Renal Cell Carcinoma: Association with Oncogenic Proteins Status." *Ann Surg Oncol* 23(2): 694-702.
12. Wang, A., H. Y. Wang, Y. Liu, M. C. Zhao, H. J. Zhang, Z. Y. Lu, Y. C. Fang, X. F. Chen and G. T. Liu (2015).

"The prognostic value of PD-L1 expression for non-small cell lung cancer patients: a meta-analysis." *Eur J Surg Oncol* 41(4): 450-456.

13. Wu, C., Y. Zhu, J. Jiang, J. Zhao, X. G. Zhang and N. Xu (2006). "Immunohistochemical localization of programmed death-1 ligand-1 (PD-L1) in gastric carcinoma and its clinical significance." *Acta Histochem* 108(1): 19-24.

14. Xu, F., L. Xu, Q. Wang, G. An, G. Feng and F. Liu (2015). "Clinicopathological and prognostic value of programmed death ligand-1 (PD-L1) in renal cell carcinoma: a meta-analysis." *Int J Clin Exp Med* 8(9): 14595-14603.

15. Zhang, Y, S. Kang, J. Shen, J. He, L. Jiang, W. Wang, Z. Guo, G. Peng, G. Chen, J. He and W. Liang (2015). "Prognostic significance of programmed cell death 1 (PD-1) or PD-1 ligand 1 (PD-L1) Expression in epithelial-originated cancer: a meta-analysis." *Medicine (Baltimore)* 94(6): e515.

What is claimed is:

1. An anti-PD-L1 antibody, or an antigen-binding fragment thereof, comprising:
   a heavy-chain variable region comprising three heavy-chain complementarity-determining regions, HCDR1, HCDR2, and HCDR3, with the sequences of SEQ ID NOs: 2-4, or 6-8, or 10-12, or 14-16, or 18-20; and
   a light-chain variable region comprising three light-chain complementarity-determining regions, LCDR1, LCDR2, and LCDR3, with the sequences of SEQ ID NOs: 22-24, or 26-28, or 30-32, or 34-36, or 38-40.

2. The anti-PD-L1 antibody, or the antigen-binding fragment thereof, according to claim 1, wherein
   the HCDR1 has the sequence of SEQ ID NO: 2, the HCDR2 has the sequence of SEQ ID NO: 3, and the HCDR3 has the sequence of SEQ ID NO: 4, and the LCDR1 has the sequence of SEQ ID NO: 22, the LCDR2 has the sequence of SEQ ID NO: 23, and the LCDR3 has the sequence of SEQ ID NO: 24; or
   the HCDR1 has the sequence of SEQ ID NO: 6, the HCDR2 has the sequence of SEQ ID NO: 7, and the HCDR3 has the sequence of SEQ ID NO: 8, and the LCDR1 has the sequence of SEQ ID NO: 26, the LCDR2 has the sequence of SEQ ID NO: 27, and the LCDR3 has the sequence of SEQ ID NO: 28; or the HCDR1 has the sequence of SEQ ID NO: 10, the HCDR2 has the sequence of SEQ ID NO: 11, and the HCDR3 has the sequence of SEQ ID NO: 12, and the LCDR1 has the sequence of SEQ ID NO: 30, the LCDR2 has the sequence of SEQ ID NO: 31, and the LCDR3 has the sequence of SEQ ID NO: 32; or the HCDR1 has the sequence of SEQ ID NO: 14, the HCDR2 has the sequence of SEQ ID NO: 15, and the HCDR3 has the sequence of SEQ ID NO: 16, and the LCDR1 has the sequence of SEQ ID NO: 34, the LCDR2 has the sequence of SEQ ID NO: 35, and the LCDR3 has the sequence of SEQ ID NO: 36; or the HCDR1 has the sequence of SEQ ID NO: 18, the HCDR2 has the sequence of SEQ ID NO: 19, and the HCDR3 has the sequence of SEQ ID NO: 20, and the LCDR1 has the sequence of SEQ ID NO: 38, the LCDR2 has the sequence of SEQ ID NO: 39, and the LCDR3 has the sequence of SEQ ID NO: 40.

3. The anti-PD-L1 antibody, or the antigen-binding fragment thereof, according to claim 1, wherein
   a. the heavy-chain variable region comprises the sequence of SEQ ID NOs: 1, 5, 9, 13, or 17, or a sequence with at least 95% homology to the sequence of SEQ ID NOs: 1, 5, 9, 13, or 17; and/or
   b. the light-chain variable region comprises the sequence of SEQ ID NOs: 21, 25, 29, 33, or 37, or a sequence with at least 95% homology to the sequence of SEQ ID NOs: 21, 25, 29, 33, or 37.

4. The anti-PD-L1 antibody, or the antigen-binding fragment thereof, according to claim 3, wherein
   a. the heavy-chain variable region comprises the sequence of SEQ ID NO: 1, or a sequence with at least 95% homology thereto and the light-chain variable region comprises the sequence of SEQ ID NO: 21, or a sequence with at least 95% homology thereto; or
   b. the heavy-chain variable region comprises the sequence of SEQ ID NO: 5, or a sequence with at least 95% homology thereto and the light-chain variable region comprises the sequence of SEQ ID NO: 25, or a sequence with at least 95% homology thereto; or
   c. the heavy-chain variable region comprises the sequence of SEQ ID NO: 9, or a sequence with at least 95% homology thereto and the light-chain variable region comprises the sequence of SEQ ID NO: 29, or a sequence with at least 95% homology thereto; or
   d. the heavy-chain variable region comprises the sequence of SEQ ID NO: 13, or a sequence with at least 95% homology thereto and the light-chain variable region comprises the sequence of SEQ ID NO: 33, or a sequence with at least 95% homology thereto; or
   e. the heavy-chain variable region comprises the sequence of SEQ ID NO: 17, or a sequence with at least 95% homology thereto and the light-chain variable region comprises the sequence of SEQ ID NO: 37, or a sequence with at least 95% homology thereto.

5. The anti-PD-L1 antibody, or the antigen-binding fragment thereof, according to claim 1, wherein the antibody or antigen-binding fragment thereof inhibits a PD-L1-mediated signal.

6. The anti-PD-L1 antibody, or the antigen-binding fragment thereof, according to claim 1, further comprising a drug conjugate covalently linked to the antibody, or the antigen-binding fragment thereof, to form an antibody-drug conjugate (ADC).

7. The anti-PD-L1 antibody, or the antigen-binding fragment thereof, according to claim 1, wherein the antibody, or the antigen-binding fragment thereof, is linked with a second antibody binding fragment to form a bispecific antibody.

8. A method for treating a cancer mediated by PD-1 or PD-L1, comprising:
   administering to a subject in need thereof a pharmaceutical composition comprising the anti-PD-L1 antibody, or the antigen-binding fragment thereof, according to claim 1.

9. The method of claim 8, wherein the cancer is lung cancer, breast cancer, prostate cancer, or colorectal cancer.

10. A method for detecting expression of PD-L1, comprising contacting a sample with the anti-PD-L1 antibody, or the antigen-binding fragment thereof, according to claim 1, and comparing a measurement of PD-L1 and the anti-PD-L1 antibody binding to a background measurement, wherein if the measurement of PD-L1 and the anti-PD-L1 antibody binding is greater than the background measurement, expression of PD-L1 is indicated.

11. The method of claim 8, wherein
   the HCDR1 has the sequence of SEQ ID NO: 2, the HCDR2 has the sequence of SEQ ID NO: 3, and the HCDR3 has the sequence of SEQ ID NO: 4, and the LCDR1 has the sequence of SEQ ID NO: 22, the LCDR2 has the sequence of SEQ ID NO: 23, and the LCDR3 has the sequence of SEQ ID NO: 24; or the HCDR1 has the sequence of SEQ ID NO: 6, the HCDR2 has the sequence of SEQ ID NO: 7, and the HCDR3 has the sequence of SEQ ID NO: 8, and the LCDR1 has the sequence of SEQ ID NO: 26, the LCDR2 has the sequence of SEQ ID NO: 27, and the LCDR3 has the sequence of SEQ ID NO: 28; or the HCDR1 has the sequence of SEQ ID NO: 10, the HCDR2 has the sequence of SEQ ID NO: 11, and the HCDR3 has the sequence of SEQ ID NO: 12, and the LCDR1 has the sequence of SEQ ID NO: 30, the LCDR2 has the sequence of SEQ ID NO: 31, and the LCDR3 has the sequence of SEQ ID NO: 32; or the HCDR1 has the sequence of SEQ ID NO: 14, the HCDR2 has the sequence of SEQ ID NO: 15, and the HCDR3 has the sequence of SEQ ID NO: 16, and the LCDR1 has the sequence of SEQ ID NO: 34, the LCDR2 has the sequence of SEQ ID NO: 35, and the LCDR3 has the sequence of SEQ ID NO: 36; or the HCDR1 has the sequence of SEQ ID NO: 18, the HCDR2 has the sequence of SEQ ID NO: 19, and the HCDR3 has the sequence of SEQ ID NO: 20, and the LCDR1 has the sequence of SEQ ID NO: 38, the LCDR2 has the sequence of SEQ ID NO: 39, and the LCDR3 has the sequence of SEQ ID NO: 40.

12. The method of claim 8, wherein
   a. the heavy-chain variable region comprises the sequence of SEQ ID NOs: 1, 5, 9, 13, or 17, or a sequence with at least 95% homology to the sequence of SEQ ID NOs: 1, 5, 9, 13, or 17; and/or
   b. the light-chain variable region comprises the sequence of SEQ ID NOs: 21, 25, 29, 33, or 37, or a sequence with at least 95% homology to the sequence of SEQ ID NOs: 21, 25, 29, 33, or 37.

13. The method of claim 8, wherein
   a. the heavy-chain variable region comprises the sequence of SEQ ID NO: 1, or a sequence with at least 95% homology thereto and the light-chain variable region comprises the sequence of SEQ ID NO: 21, or a sequence with at least 95% homology thereto; or b. the heavy-chain variable region comprises the sequence of SEQ ID NO: 5, or a sequence with at least 95% homology thereto and the light-chain variable region comprises the sequence of SEQ ID NO: 25, or a sequence with at least 95% homology thereto; or
c. the heavy-chain variable region comprises the sequence of SEQ ID NO: 9, or a sequence with at least 95% homology thereto and the light-chain variable region comprises the sequence of SEQ ID NO: 29, or a sequence with at least 95% homology thereto; or
d. the heavy-chain variable region comprises the sequence of SEQ ID NO: 13, or a sequence with at least 95% homology thereto and the light-chain variable region comprises the sequence of SEQ ID NO: 33, or a sequence with at least 95% homology thereto; or
e. the heavy-chain variable region comprises the sequence of SEQ ID NO: 17, or a sequence with at least 95% homology thereto and the light-chain variable region comprises the sequence of SEQ ID NO: 37, or a sequence with at least 95% homology thereto.

14. The method of claim 8, wherein the antibody, or the antigen-binding fragment thereof, comprises a drug conjugate covalently linked to the antibody, or the antigen-binding fragment thereof, to form an antibody-drug conjugate (ADC).

15. The method of claim 8, wherein the antibody, or the antigen-binding fragment thereof, is linked with a second antibody binding fragment to form a bispecific antibody.

\* \* \* \* \*